United States Patent
Kaufold et al.

(10) Patent No.: US 10,093,811 B2
(45) Date of Patent: Oct. 9, 2018

(54) ANTIMICROBIAL SACRIFICIAL FLOOR COATING SYSTEMS

(71) Applicant: Spartan Chemical Company, Inc., Maumee, OH (US)

(72) Inventors: Rebecca S. Kaufold, Perrysburg, OH (US); Jason J. Welch, Whitehouse, OH (US); Jamie N. Venable, Perrysburg, OH (US)

(73) Assignee: SPARTAN CHEMICAL COMPANY, INC., Maumee, OH (US)

( * ) Notice: Subject to any disclaimer, the term of this patent is extended or adjusted under 35 U.S.C. 154(b) by 21 days.

(21) Appl. No.: 15/602,508

(22) Filed: May 23, 2017

(65) Prior Publication Data

US 2018/0009995 A1 Jan. 11, 2018

Related U.S. Application Data

(60) Provisional application No. 62/360,740, filed on Jul. 11, 2016, provisional application No. 62/400,437, filed on Sep. 27, 2016, provisional application No. 62/504,165, filed on May 10, 2017.

(51) Int. Cl.

| | |
|---|---|
| *C09D 5/14* | (2006.01) |
| *C09D 9/00* | (2006.01) |
| *C09D 9/04* | (2006.01) |
| *C09D 133/00* | (2006.01) |
| *A01N 25/10* | (2006.01) |
| *A01N 47/44* | (2006.01) |
| *C08L 3/08* | (2006.01) |

(52) U.S. Cl.
CPC ............ *C09D 5/14* (2013.01); *A01N 25/10* (2013.01); *A01N 47/44* (2013.01); *C08L 3/08* (2013.01); *C09D 9/005* (2013.01); *C09D 9/04* (2013.01); *C09D 133/00* (2013.01)

(58) Field of Classification Search
CPC ...... C09D 5/14; C09D 133/12; C09D 175/16; A01N 47/44
USPC ........................................................ 427/299
See application file for complete search history.

(56) References Cited

U.S. PATENT DOCUMENTS

| | | | |
|---|---|---|---|
| 5,035,829 A | 7/1991 | Suwala | |
| 5,049,300 A | 9/1991 | Fusiak et al. | |
| 6,180,584 B1 | 1/2001 | Sawan et al. | |
| 6,270,754 B1 | 8/2001 | Zhou et al. | |
| 6,432,395 B1 | 8/2002 | Rochon et al. | |
| 6,448,305 B1 | 9/2002 | Watterson, III et al. | |
| 6,465,412 B1 | 10/2002 | Mahieu et al. | |
| 6,730,654 B2 | 5/2004 | Godfroid et al. | |
| 6,762,162 B1 | 7/2004 | Valpey, III et al. | |
| 7,094,741 B2 | 8/2006 | Barnabas et al. | |
| 7,118,785 B2 | 10/2006 | Rogmann et al. | |
| 7,217,759 B2 | 5/2007 | Hodge et al. | |
| 7,226,968 B2 | 6/2007 | Hodge et al. | |
| 7,288,264 B1 | 10/2007 | Sawan et al. | |
| 7,699,941 B2 | 4/2010 | Pivonka et al. | |
| 7,713,472 B2 | 5/2010 | Raad et al. | |
| 7,956,026 B2 | 6/2011 | Kobayashi et al. | |
| 7,981,946 B2 | 7/2011 | Krishnan | |
| 7,994,251 B2 | 8/2011 | Rogmann et al. | |
| 8,093,199 B2 | 1/2012 | Johnson et al. | |
| 8,124,169 B2 | 2/2012 | Ylitalo et al. | |
| 8,168,578 B2 | 5/2012 | Serobian | |
| 8,232,238 B2 | 7/2012 | Ochomogo et al. | |
| 8,309,626 B2 | 11/2012 | Chen et al. | |
| 8,603,453 B2 | 12/2013 | Hodge et al. | |
| 8,753,692 B2 | 6/2014 | Gawande et al. | |
| 8,785,679 B2 * | 7/2014 | Brizius ................ | C09D 133/12 106/15.05 |
| 9,247,736 B2 | 2/2016 | Ylitalo et al. | |
| 2003/0224030 A1 | 12/2003 | Uchiyama et al. | |
| 2005/0014670 A1 | 1/2005 | Hodge et al. | |

(Continued)

FOREIGN PATENT DOCUMENTS

| | | |
|---|---|---|
| EP | 1290121 B1 | 4/2004 |
| EP | 1633192 B1 | 11/2004 |
| EP | 1624755 A1 | 2/2006 |
| EP | 2407028 A1 | 1/2012 |

(Continued)

OTHER PUBLICATIONS

Gustavo F. de Paula et al. "Physical and Chemical Characterization of Poly(hexamethylene biguanide) Hydrochloride", Polymers, vol. 3, No. 4, p. 928-941, Jun. 1, 2011 (14 pages).

*Primary Examiner* — Gregory E Webb

(74) *Attorney, Agent, or Firm* — Shumaker, Loop & Kendrick, LLP

(57) ABSTRACT

Disclosed are antimicrobial sacrificial floor coatings systems including an antimicrobial sacrificial floor coating composition capable of reducing and/or preventing gram positive and gram negative bacterial growth on floors. Also disclosed is an antimicrobial sacrificial floor coating remover being readily capable of removing the antimicrobial sacrificial floor coating as desired from previously treated flooring surfaces. In certain aspects, the antimicrobial sacrificial floor coatings can include a nonionic acrylic polymer; a nonionic wax; and a cationic alkyl biguanide or salt thereof. The antimicrobial sacrificial floor coating may further include a cationic wax that further stabilizes the system during storage, application, and/or post-application to a floor surface. The antimicrobial sacrificial floor coating composition has a pH of less than 7 while exhibiting continuous antimicrobial properties from full cure on a floor surface up to 1 year post-application to the floor surface at a minimum contact time of 1 hour.

44 Claims, No Drawings

(56) References Cited

U.S. PATENT DOCUMENTS

| | | | |
|---|---|---|---|
| 2005/0080158 A1* | 4/2005 | Ong | A01N 25/10 523/122 |
| 2008/0026026 A1 | 1/2008 | Lu et al. | |
| 2009/0247485 A1 | 10/2009 | Ahmed et al. | |
| 2012/0148751 A1* | 6/2012 | Herdt | C09D 5/14 427/299 |
| 2013/0209536 A1 | 8/2013 | Krogman et al. | |
| 2014/0190004 A1 | 7/2014 | Riall et al. | |

FOREIGN PATENT DOCUMENTS

| | | |
|---|---|---|
| WO | 2004100663 A1 | 11/2004 |
| WO | 2004100664 A1 | 11/2004 |
| WO | 2014093578 A1 | 6/2014 |
| WO | 2016040529 A1 | 3/2016 |

* cited by examiner

ANTIMICROBIAL SACRIFICIAL FLOOR COATING SYSTEMS

TECHNICAL FIELD

The present invention relates generally to the field of floor coating systems, and more particularly, to antimicrobial sacrificial floor coatings capable of reducing and/or preventing gram positive and gram negative bacteria growth for extended time periods on flooring surfaces for pedestrian traffic. Also disclosed are compositions for removing these antimicrobial sacrificial floor coatings as desired by a user of the system.

BACKGROUND

U.S. Pat. No. 8,124,169 discloses an antimicrobial coating system that can be applied to "high touch" surfaces including, for example, counters, tables, and sinks to temporarily disinfect these surfaces by reducing microbial growth. However, these formulations are susceptible to removal by slight and/or moderate frictional forces. Thus, the formulations disclosed in U.S. Pat. No. 8,124,169 have at best temporary antimicrobial activity, but should not be applied to floors due to high pedestrian traffic volume and frictional forces applied thereto that would easily remove these formulations thereby limiting and/or greatly reducing antimicrobial efficacy.

In contrast to the formulations disclosed in U.S. Pat. No. 8,124,169 that can merely withstand slight and/or moderate frictional forces, certain floor coating compositions utilize prepolymers, cross-linking agents, and antimicrobial agents (e.g., including ionic zinc, silver, and/or copper) that polymerize and/or cross-link when applied to flooring surfaces thereby forming a more permanent coating than those disclosed in U.S. Pat. No. 8,124,169. Even though these systems form permanent coatings, these systems may lose antimicrobial properties/efficacy over time, which leads to an increased presence of gram positive and/or gram negative bacteria (e.g., pathogenic gram positive and/or gram negative bacteria) over time. Thus, even though these formulations are supposedly permanent, these coatings should be removed and re-applied periodically to adequately control and/or prevent microbial growth on surfaces to which these formulations are applied. However, due to the above mentioned polymerization and/or cross-linking processes, removal of these permanent floor systems is very difficult, dangerous, and labor intensive—often requiring application of strong solvent stripping solutions (e.g., highly basic stripping solutions that re-liquefy the coatings) and/or physical grinding processes.

In addition, to the above mentioned problems associated with current antimicrobial compositions, many of the coating formulations known in the art further include unfavorable chemistry that may counteract the antimicrobial agent(s) thereby greatly reducing and, in some instances, even eliminating the antimicrobial properties associated with these formulation's antimicrobial agent.

SUMMARY

Therefore, it is an object of the invention to provide antimicrobial sacrificial floor coating systems including (1) an antimicrobial sacrificial floor coating composition for application to floors and (2) a solution for removing the antimicrobial sacrificial floor coating as desired. These systems are specifically formulated to overcome the above mentioned problems. These antimicrobial sacrificial floor coating(s) can preferably withstand high frictional forces associated with heavy pedestrian traffic volume on a flooring surface while concurrently providing extended antimicrobial properties/efficacy thereby preventing and/or reducing gram positive and/or gram negative bacteria growth on these high traffic surfaces for extended periods of time. These antimicrobial sacrificial floor coating(s) are also considerably easier to remove than the above mentioned permanent floor coatings due to the lack of polymerizable prepolymers, cross-linking agents, or a combination thereof. As disclosed further below, the system also includes a solution for removing the antimicrobial sacrificial floor coating from a treated floor as desired. This antimicrobial sacrificial floor coating remover is preferably an acidic solution that intercalates and swells the antimicrobial sacrificial floor coating during a predetermined dwell time thereby allowing for removal of the antimicrobial sacrificial floor coating from a floor surface via subsequent scrubbing or use of a low speed floor machine (i.e., application of physical/mechanical force).

A first object of the present invention is consequently an antimicrobial sacrificial floor coating composition(s) comprising a nonionic acrylic polymer; a nonionic wax; a cationic wax; and an antimicrobial agent that includes a cationic alkyl biguanide or salt thereof, wherein the antimicrobial sacrificial floor coating composition has a pH of less than 7. Preferably, the antimicrobial sacrificial floor coating composition according to the invention is an aqueous solution. The antimicrobial sacrificial floor coating composition is adapted to cure on a floor surface in about 30 to 60 minutes at a humidity ranging from 20% to 80% thereby forming a clear (e.g., transparent and/or translucent), thin film coating on the floor that exhibits continuous sanitization (i.e., antimicrobial properties) from full cure on the floor surface up to 6 months post-application (or in certain instances up to 1 year post-application) on floor surfaces having light, moderate, and heavy pedestrian traffic. In certain aspects, the antimicrobial sacrificial floor coating composition is adapted to exhibit a log reduction from 3.3 to 5.75 for gram negative bacteria (e.g., *E. coli* and/or *P. aeruginosa*, etc.) and a log reduction from 3.11 to 6.3 for gram positive bacteria (e.g., *S. aureus*) at 1 hour post application of a bacterial inoculum, 2 hours post application of a bacterial inoculum, 4 hours post application of a bacterial inoculum, 6 hours post application of a bacterial inoculum, and/or 24 hours post application of a bacterial inoculum to a floor surface having the antimicrobial sacrificial floor coating composition applied (cured) thereon. As alluded to above, the coating composition is adapted to exhibit these antimicrobial properties from full cure on the floor surface preferably up to 6 months and more preferably up to 1 year at a minimum contact time of one hour on the cured coating. In other words, the coating composition kills at least 99% and more preferably at least 99.9% of gram positive and gram negative bacteria when in contact with the cured coating for at least one hour. In certain aspects, antimicrobial activity of the clear (e.g., transparent and/or translucent), thin film coating formed by the antimicrobial sacrificial floor coating composition to the floor is based on the resulting clear, thin film having a thickness ranging from 0.2 mils to 1.1 mils, more preferably from 0.25 mils to 0.7 mils. The antimicrobial sacrificial floor coating compositions may further include various additives and diluents including, for example, water, coalescing solvents, wetting agents, leveling agents, or any combination thereof. It should be further noted that these antimicrobial sacrificial floor coating composition(s) preferably maintain stability (e.g., no or limited viscosity increases—preferably maintaining a viscosity ranging from 3 to 6 cP, antimicrobial activity, etc.) when exposed to high temperatures for prolonged periods of time (e.g., exposed to 120° F. for 20, 30, or 40 days) and further maintain such stability during and post-application to a floor. An antimicrobial sacrificial floor coating composition of the invention is in particular heat stable and maintains a viscosity ranging from 6 to 6 cP when exposed to 120° F. for 20 to 30 days. Post-application to the floor, these compositions immediately begin reducing growth and/or preventing growth of gram positive and gram negative bacteria and exhibit continuous antimicrobial efficacy/growth inhibitory activity for extended periods of time. For example, in certain aspects, the disclosed antimicrobial sacrificial floor coating compositions exhibit and maintain antimicrobial efficacy for at least one month, preferably at least two months, preferably at least three months, more preferably at least four months, even more preferably up to six months, and most preferably up to 1 year post-application on flooring surfaces having light, moderate, and heavy pedestrian traffic. Because the disclosed antimicrobial floor coating is a sacrificial coating, longevity of the antimicrobial properties is dependent on traffic volume and maintenance. In a particular embodiment, the antimicrobial sacrificial floor coating composition of the invention consists of a nonionic acrylic polymer at a concentration ranging from 30 to 40 wt % of the antimicrobial sacrificial floor coating composition; a nonionic wax at a concentration ranging from 2.5 to 8 wt % of the antimicrobial sacrificial floor coating composition; a cationic wax at a concentration ranging from 2.5 to 8 wt % of the antimicrobial sacrificial floor coating composition; an antimicrobial agent that includes a cationic alkyl biguanide or salt thereof, the antimicrobial agent being present at a concentration of up to 4 wt % of the antimicrobial sacrificial floor coating composition; water at a concentration ranging from 30 to 65 wt % of the antimicrobial sacrificial floor coating composition; and at least one additive, wherein the antimicrobial sacrificial floor coating composition has a pH of less than 7.

In certain aspects, the nonionic wax is a nonionic alkylene polymer and/or emulsions including the nonionic alkylene polymer. The nonionic wax is in particular a nonionic alkylene polymer. The nonionic alkylene polymer may be polyethylene or derivative thereof, polypropylene or derivative thereof, or a combination thereof. For example, the nonionic alkylene polymer may be a nonionic oxidized polyethylene, a nonionic oxidized polypropylene, or a combination thereof.

In certain aspects, the nonionic wax may be a high density nonionic alkylene polymer. Accordingly, the nonionic wax can for example be high density polyethylene, high density polypropylene, or a combination thereof. The high density polyethylene can preferably be a nonionic oxidized high density polyethylene, and the high density polypropylene can preferably be a nonionic oxidized high density polypropylene. A nonionic wax according to the invention can in particular be a high density polyethylene or derivative thereof, high density polypropylene or derivative thereof, or a combination thereof, more particularly an oxidized high density polyethylene.

In certain aspects, the nonionic wax may be present in the antimicrobial sacrificial floor coating composition at a concentration of between 2 wt % and 12 wt %, more preferably between 2.5 wt % and 8 wt %, and most preferably from 2.75 wt % to 4 wt % of the antimicrobial sacrificial floor coating composition. For example, high density polyethylene, high density polypropylene, or a combination thereof may be used in the disclosed formulations at a concentration between 2 wt % and 12 wt % of the overall composition. In certain preferred aspects, the nonionic wax is high density polyethylene (e.g., nonionic oxidized high density polyethylene) at a concentration of between 2 wt % and 12 wt %, more preferably between 2.5 wt % and 8 wt %, and most preferably from 2.75 wt % to 4 wt % and has a molecular weight ranging between 9,000-10,000 g/mol. Accordingly, in a preferred embodiment, the antimicrobial sacrificial floor coating composition of the invention is such that the nonionic wax is an oxidized high density polyethylene and is at a concentration of between 2.5 wt % and 8 wt % of the antimicrobial sacrificial floor coating composition and has a molecular weight ranging between 9,000 to 10,000 g/mol.

In certain aspects, the cationic wax is a cationic alkylene polymer and/or an emulsion including the cationic alkylene polymer. The cationic wax is in particular a cationic alkylene polymer. For example, the cationic alkylene polymer may be cationic oxidized alkylene(s) and/or emulsions including cationic oxidized alkylene(s). The cationic alkylene polymer may preferably be an oxidized polyethylene, oxidized polypropylene, or a combination thereof. In certain aspects, the cationic wax is an emulsion including high density oxidized polyethylene wax. In preferred embodiments, the cationic alkylene polymer is an oxidized high density polyethylene, an oxidized high density oxidized polypropylene or a combination thereof.

In certain aspects, the cationic wax may include a cationic emulsion of an oxidized high density alkylene polymer. Accordingly, the cationic wax can for example be high density polyethylene, high density polypropylene, or a combination thereof. The cationic alkylene polymer can preferably be a cationic oxidized high density polyethylene, a cationic oxidized high density polypropylene, or a combination thereof.

In certain aspects, the cationic wax may be present in the antimicrobial sacrificial floor coating composition at a concentration of between 2 wt % and 12 wt %, more preferably between 2.5 wt % and 8 wt %, and most preferably from 2.75 wt % to 5.0 wt % of the antimicrobial sacrificial floor coating composition. For example, high density polyethylene (e.g., cationic oxidized high density polyethylene), high density polypropylene (e.g., cationic oxidized high density polypropylene), or a combination thereof may be used in the disclosed formulations at a concentration between 2 wt % and 12 wt %, preferably between 2.5 wt % and 8 wt %, and most preferably from 2.75 wt % to 5.0 wt % of the overall composition. In certain preferred aspects, the cationic wax is a cationic oxidized, high density polyethylene at a concentration of between 2.5 wt % and 8 wt % and has a molecular weight ranging preferably between 1,000 and 50,000 g/mol and more preferably between 5,000 and 15,000 g/mol. Accordingly, in a preferred embodiment, the antimicrobial sacrificial floor coating composition of the invention is such that the cationic wax is a cationic oxidized high density polyethylene at a concentration of between 2.5 wt % and 8.0 wt % of the antimicrobial sacrificial floor coating composition and has a molecular weight ranging from 1,000 to 50,000 g/mol. In certain aspects, the ratio of cationic wax to nonionic wax in the antimicrobial sacrificial floor coating composition ranges from 1.25:1 to 1:1.25, more preferably the ratio of cationic wax to nonionic wax in the antimicrobial sacrificial floor coating composition is 1:1.

In certain aspects, the cationic alkyl biguanide or salt thereof is polyhexamethylene biguanide, polyaminopropryl biguanide, or a combination thereof. The cationic alkyl biguanide or salt thereof ranges from 0.4 to 1 active wt %, preferably from 0.5 to 0.95 active wt %, more preferably from 0.6 to 0.95 active wt %, more preferably from 0.65 to 0.95 active wt %, and most preferably from 0.74 to 0.95 active wt % of the antimicrobial sacrificial floor coating composition.

In certain aspects, the antimicrobial sacrificial floor coating composition does not include crosslinking agents and is not polymerizable during or post-application to the floor surface.

In certain aspects, the nonionic acrylic polymer is a non-crosslinked, nonionic acrylic polymer.

Another object of the present invention is an antimicrobial sacrificial floor coating remover for removing the disclosed antimicrobial sacrificial coatings from the floor obtained with an antimicrobial sacrificial floor coating composition according to the invention (flooring surface and/or substrate) as desired by a user of the system. The antimicrobial sacrificial floor coating remover of the invention comprises an organic solvent at a concentration ranging from 17 wt % to 30 wt % of the antimicrobial sacrificial floor coating remover; a nonionic surfactant at an effective concentration for aiding in wetting and increasing water solubility of the organic solvent in the antimicrobial sacrificial floor coating remover, in particular at a concentration ranging from 0.5 wt % to 5 wt % of the antimicrobial sacrificial floor coating remover; and an organic acid at a concentration ranging from 1 wt % to 5 wt % of the antimicrobial sacrificial floor coating remover, wherein pH of the antimicrobial sacrificial floor coating remover is acidic.

In preferred embodiments, the antimicrobial sacrificial coating remover of the invention further comprises water, which may be present at a concentration ranging from 60 wt % to 80 wt % of the antimicrobial sacrificial floor coating remover.

In certain aspects, the pH of the antimicrobial sacrificial floor coating remover ranges from 2 to 3.5.

In certain aspects, the organic acid of the antimicrobial sacrificial floor coating remover comprises a lower alkyl carboxylic acid moiety. In certain aspects, the lower alkyl carboxylic acid moiety is R—COOH in which R is hydrogen, a linear or branched C1-C6 alkyl, a primary alcohol, or a secondary alcohol. For example, the organic acid may be, formic acid, acetic acid, propanoic acid or derivatives thereof, butyric acid or derivatives thereof, valeric acid or derivatives thereof, or caproic acid or derivatives thereof.

In certain aspects, the organic acid of the antimicrobial sacrificial floor coating remover is preferably propanoic acid or a derivative thereof, preferably lactic acid and more preferably L-lactic acid.

In certain aspects, the organic acid of the antimicrobial sacrificial floor coating remover is lactic acid, and more preferably, L-lactic acid at a concentration ranging from 1 to 5 wt % of the antimicrobial sacrificial floor coating remover.

In certain aspects, the nonionic surfactant of the antimicrobial sacrificial floor coating remover comprises a linear alcohol ethoxylate, preferably at a concentration ranging from 0.5 wt % to 5 wt % of the antimicrobial sacrificial floor coating remover.

In certain aspects, the linear alcohol ethoxylate of the antimicrobial sacrificial floor coating remover is a C9-C11 linear alcohol ethoxylate.

In certain aspects, the organic solvent of the antimicrobial sacrificial floor coating remover includes a first organic solvent that is a glycol ether at a concentration ranging from 16 to 25 wt % of the antimicrobial sacrificial floor coating remover and a second organic solvent at a concentration ranging from 1 to 7 wt % of the antimicrobial sacrificial floor coating remover.

In certain aspects, the glycol ether of the antimicrobial sacrificial floor coating remover is diethylene glycol monobutyl ether. In certain aspects, the second organic solvent included in the organic solvent of the antimicrobial sacrificial floor coating remover is butan-1-yl-3-hydroxybutanoate. In a particular embodiment, the glycol ether of the antimicrobial sacrificial floor coating remover is diethylene glycol monobutyl ether and the second organic solvent included in the organic solvent of the antimicrobial sacrificial floor coating remover is butan-1-yl-3-hydroxybutanoate.

In certain aspects, the antimicrobial sacrificial floor coating remover has a zero volatile organic compound content (0 VOC).

Also disclosed is a kit comprising the antimicrobial sacrificial floor coating composition according to the invention and the antimicrobial sacrificial floor coating remover according to the invention. In certain aspects, the kit includes the antimicrobial sacrificial floor coating composition within a first container, and the antimicrobial sacrificial floor coating remover within a second container. Accordingly, another object of the present invention is a kit comprising an antimicrobial sacrificial floor coating composition according to the invention in a first container and an antimicrobial sacrificial floor coating remover according to the invention in a second container. While stored in the first container, these antimicrobial sacrificial floor coating composition(s) preferably maintains stability (e.g., no or limited viscosity increases—the composition preferably maintains a viscosity ranging from 4 to 6 cP, no or limited loss in antimicrobial activity, etc.) when exposed to high temperatures for prolonged periods of time (e.g., exposed to 120° F. for 20, 30, or 40 days) and further maintains such stability during and post-application to a floor for the time periods disclosed herein. The antimicrobial sacrificial floor coating remover is configured to remove the antimicrobial sacrificial floor coating from a flooring surface. Accordingly, another object of the present invention is the use of the antimicrobial sacrificial floor coating remover of the invention to remove the antimicrobial sacrificial floor coating of the invention from a surface post-application of the antimicrobial sacrificial floor coating of the invention.

In certain aspects, the antimicrobial sacrificial floor coating composition(s) of the kit includes a nonionic acrylic polymer; a nonionic wax; a cationic wax; and an antimicrobial agent that includes a cationic alkyl biguanide or salt thereof, wherein the antimicrobial sacrificial floor coating composition is an aqueous solution and has a pH of less than 7. The antimicrobial sacrificial floor coating is adapted to cure on a floor surface in about 30 to 60 minutes at a humidity ranging from 20% to 80% thereby forming a clear, thin film coating having a thickness ranging from 0.2 mils to 1.1 mils, more preferably from 0.25 mils to 0.7 mils that exhibits continuous sanitization (i.e., antimicrobial properties) from full cure of the coating up to 6 months post-application (or in certain instances up to 1 year post-application) on flooring surfaces having light, moderate, and heavy pedestrian traffic. Accordingly, another object of the present invention is the use of the antimicrobial sacrificial floor coating composition of the invention in order to form a clear, thin film coating having a thickness ranging from 0.2 mils to 1.1 mils that exhibits continuous antimicrobial properties from full cure on a floor surface up to 1 year post-application to the floor surface at a minimum contact time of 1 hour. The antimicrobial sacrificial floor coating composition of the invention is moreover adapted to exhibit a log reduction of from 3.3 to 5.75 for gram negative bacteria (e.g., *E. coli* and/or *P. aeruginosa*, etc.) and a log reduction of 3.11 to 6.3 for gram positive bacteria (e.g., *S. aureus*) at 1 hour post application of a bacterial inoculum, 2 hours post application of a bacterial inoculum, 4 hours post application of a bacterial inoculum, 6 hours post application of a bacterial inoculum, and/or 24 hours post application of a bacterial inoculum to a floor surface having the antimicrobial sacrificial floor coating composition applied (cured) thereon. Accordingly, another object of the present invention is the use of the antimicrobial sacrificial floor coating composition according to the invention in order to form a clear, thin film coating having a thickness ranging from 0.2 mils to 1.1 mils that exhibits continuous antimicrobial properties from full cure on a floor surface up to 1 year post-application to the floor surface at a minimum contact time of 1 hour, wherein the antimicrobial sacrificial floor coating composition exhibits a log reduction of from 3.3 to 6 for gram negative bacteria and a log reduction of from 3.11 to 6.3 for gram positive bacteria after full cure on the flooring surface and at a minimum contact time of 1 hour with the coating composition. The coating composition preferably kills at least 99% and more preferably at least 99.9% of gram positive and gram negative bacteria when in contact with the cured coating for at least one hour. The antimicrobial sacrificial floor coating composition in the kit preferably exhibits antimicrobial efficacy for at least one month, preferably at least two months, preferably at least three months, more preferably at least four months, more preferably up to six months, and most preferably up to 1 year post-application on flooring surfaces having light, moderate, and heavy pedestrian traffic with a minimum contact time of one hour.

In certain aspects, the antimicrobial sacrificial floor coating remover of the kit includes an organic solvent at a concentration ranging from 17 wt % to 30 wt % of the antimicrobial sacrificial floor coating remover; water, in particular at a concentration ranging from 60 wt % to 80 wt % of the antimicrobial sacrificial floor coating remover; a nonionic surfactant at an effective concentration for aiding in wetting and increasing water solubility of the organic solvent in the antimicrobial sacrificial floor coating remover, in particular at a concentration ranging from 0.5 wt % to 5 wt % of the antimicrobial sacrificial floor coating remover; and an organic acid at a concentration ranging from 1 wt % to 5 wt % of the antimicrobial sacrificial floor coating remover, wherein pH of the antimicrobial sacrificial floor coating remover is acidic.

In certain aspects, the antimicrobial sacrificial floor coating remover is configured to be diluted with 5 parts water to 1 part antimicrobial sacrificial floor coating remover (working solution/concentration) to remove the antimicrobial sacrificial floor coating from a flooring surface. Accordingly, the previously indicated uses according to the invention can moreover be such that the antimicrobial sacrificial floor coating remover is adapted for dilution with water at a ratio ranging from 1 part antimicrobial sacrificial floor coating remover to 7 parts water to 1 part antimicrobial sacrificial floor coating remover to 5 parts water, in particular the antimicrobial sacrificial floor coating remover is diluted with water at a ratio ranging from 1 part antimicrobial sacrificial floor coating remover to 7 parts water to 1 part antimicrobial sacrificial floor coating remover to 5 parts water, and is preferably diluted with 5 parts water to 1 part antimicrobial sacrificial floor coating remover. The antimicrobial sacrificial floor coating remover also preferably has high buffering capacity allowing the initial pH of the concentrated remover to be maintained during and after dilution with water. For example, after diluting the antimicrobial sacrificial floor coating remover with 5 parts water to 1 part antimicrobial sacrificial floor coating remover (working solution/concentration), pH of the working solution ranges from pH 2.0 to 3.0, more preferably from pH 2.35 to 2.8, or most preferably from pH 2.6 to 2.8.

In certain aspects, the antimicrobial sacrificial floor coating remover is configured to intercalate and swell the antimicrobial sacrificial floor coating within a dwell time ranging from about 5 to about 10 minutes post-application to the antimicrobial sacrificial floor coating. Accordingly, another object of the present invention relates to the use of the antimicrobial sacrificial floor coating remover of the invention to intercalate and swell the antimicrobial sacrificial floor coating within five to ten minutes post-application to the antimicrobial sacrificial floor coating while removing the antimicrobial sacrificial floor coating.

In certain aspects, the antimicrobial sacrificial floor coating remover is configured to not re-liquefy the antimicrobial sacrificial floor coating composition while removing antimicrobial sacrificial floor coating composition from the flooring surface. Accordingly, the previously indicated uses according to the invention can moreover be such that the antimicrobial sacrificial floor coating remover of the invention does not re-liquefy the antimicrobial sacrificial floor coating composition while removing the antimicrobial sacrificial floor coating composition from a surface.

In certain aspects, the antimicrobial sacrificial floor coating remover has a zero volatile organic compound content (0 VOC).

In certain aspects, disclosed is an antimicrobial sacrificial floor coating remover comprising an organic solvent at a concentration ranging from 17 wt % to 30 wt % of the antimicrobial sacrificial floor coating remover; water at a concentration ranging from 60 wt % to 80 wt % of the antimicrobial sacrificial floor coating remover; a nonionic surfactant at an effective concentration (e.g., 0.5 wt % to 5.0 wt %, 0.4 to 2.0 wt %, etc. of the antimicrobial sacrificial floor coating remover) for aiding in wetting and increasing water solubility of the organic solvent in the antimicrobial sacrificial floor coating remover, in particular at a concentration ranging from 0.5 wt % to 5 wt % of the antimicrobial sacrificial floor coating remover; and an organic acid at a concentration ranging from 1 wt % to 5 wt % of the antimicrobial sacrificial floor coating remover, wherein the concentrated antimicrobial sacrificial floor coating is preferably adapted for dilution with water at a ratio ranging from 1 part antimicrobial sacrificial floor coating to 7 parts water, more preferably 1 part concentrated antimicrobial sacrificial floor coating to 5 parts water, and pH of the antimicrobial sacrificial floor coating remover remains acidic after dilution with water (e.g., pH from 2.0 to 3.0, more preferably pH from 2.35 to 2.8, or most preferably pH from 2.6 to 2.8). In certain aspects, the nonionic surfactant is present at a concentration ranging from 0.5 wt % to 5 wt % of the concentrated antimicrobial sacrificial floor coating remover.

Embodiments of the invention can include one or more or any combination of the above features and configurations.

Additional features, aspects and advantages of the invention will be set forth in the detailed description which follows, and in part will be readily apparent to those skilled in the art from that description or recognized by practicing the invention as described herein. It is to be understood that both the foregoing general description and the following detailed description present various embodiments of the invention, and are intended to provide an overview or framework for understanding the nature and character of the invention as it is claimed. The accompanying drawings are included to provide a further understanding of the invention.

DETAILED DESCRIPTION

The present invention will now be described more fully hereinafter. It is to be understood that the aspects described below are not limited to specific compounds, synthetic methods, or uses as such may, of course, vary. It is also to be understood that the terminology used herein is for the purpose of describing particular aspects only and is not intended to be limiting. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Moreover, "mils" is a unit representing a thousandth of an inch, (i.e., 0.001 inches) that can also be referred to as "thou". Accordingly, it must be understood in the present text that one mil corresponds to 0.0254 millimeters (mm), i.e. to 25.40 micrometers (μm).

"Optional" or "optionally" means that the subsequently described event or circumstance can or cannot occur, and that the description includes instances where the event or circumstance occurs and instances where it does not.

As used herein, the term "about" is used to provide flexibility to a numerical range endpoint by providing that a given value may be "slightly above" or "slightly below" the endpoint without affecting the desired result.

The phrase "sacrificial floor coating composition", as referred to herein, means a topical coating that protects flooring substrate(s) from damage, in particular due to pedestrian traffic. The coating formed by the sacrificial floor coating composition is not permanent in nature and is designed to be removed and reapplied as dictated by surface wear. Without wishing to be bound by theory, the inventors consider that, when the sacrificial floor coating composition is used to protect flooring substrate(s) from damage due to pedestrian traffic, the sacrificial coatings extend the lifespan of floor substrate(s) by absorbing superficial traffic and preventing direct damage to the floor substrate. Removal and reapplication of the sacrificial coating restores the flooring substrate(s) appearance without requiring complete flooring substrate removal and/or reinstallation. The sacrificial floor coating composition meets at least one of the following ASTM criteria, preferably at least two of the following ASTM criteria, more preferably at least three of the following ASTM criteria, and most preferably all of the following ASTM criteria: (1) perform as well as commercially available floor finishes when tested for soil resistance according to ASTM D-3206-08 (Standard Method for Soil Resistance of Floor Polishes); (2) exhibit consistent film resistance and/or full recovery for static and dynamic water spotting according to ASTM D-1793-92 (Standard Method for Water Spotting of Emulsion Floor Polishes); (3) rates as "excellent" and/or shows no deterioration of film appearance when tested for detergent resistance according to ASTM D-3207-92 (Standard Test Method for Detergent Resistance of Floor Polish Films); and/or (4) static coefficient of friction is equal to or greater than 0.5 as measured by ASTM D-2047-11 (Standard Test Method for Static Coefficient of Friction of Polish-Coated Surfaces as Measured by the James Machine).

The phrase "dwell time" refers to a predetermined time period in which the disclosed antimicrobial sacrificial floor coating remover is applied to a flooring surface (previously treated with antimicrobial sacrificial floor coating) in order for the remover to effectively swell the antimicrobial sacrificial floor coating thereby allowing for subsequent removal of the antimicrobial sacrificial floor coating from the flooring surface.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within the ranges as if each numerical value and sub-range is explicitly recited. As an illustration, a numerical range of "about 1 to 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. as well as 1, 2, 3, 4, and 5, individually. The same principle applies to ranges reciting only one numerical value as a minimum or a maximum. Furthermore, such an interpretation should apply regardless of the breadth of the range or the characteristics being described.

The compositions and methods described herein can comprise, consist of, or consist essentially of the essential elements and limitations described herein, as well as any additional or optional ingredients, components, or limitations described herein.

It is understood that any given particular aspect of the disclosed compositions and methods can be easily compared to the specific examples and embodiments disclosed herein. By performing such a comparison, the relative efficacy of each particular embodiment can be easily determined. Particularly preferred compositions and methods are disclosed in the Examples herein, and it is understood that these compositions and methods, while not necessarily limiting, can be performed with any of the compositions and methods disclosed herein.

Disclosed are antimicrobial sacrificial floor coating systems including (1) an antimicrobial sacrificial floor coating composition for application to floors that provide antimicrobial properties/characteristics to floors for extended time periods (e.g., up to one month, up to two months, up to three months, up to four months, up to six months, up to one year) and (2) a solution for removing the antimicrobial sacrificial floor coating as desired. The disclosed antimicrobial sacrificial floor coating composition(s) are specifically formulated to be applied and coat floor surfaces and upon curing thereon to withstand high frictional forces associated for example with heavy pedestrian traffic volume and regular cleaning on a flooring surface while concurrently providing extended antimicrobial properties/efficacy to at least prevent and/or reduce gram positive and gram negative bacteria growth on these high traffic surfaces for extended periods of time. These antimicrobial sacrificial floor coating(s) are also easier to remove than currently available permanent floor coatings due to the lack of polymerizable prepolymers, cross-linking agents, etc. and are as easy to remove as currently available sacrificial floor coatings. Specifically disclosed are antimicrobial sacrificial floor coating composition(s) including a nonionic acrylic polymer; a nonionic wax; a cationic wax; and an antimicrobial agent that includes cationic alkyl biguanide or salt thereof, wherein the antimicrobial sacrificial floor coating composition is an aqueous solution and has a pH less than 7. The antimicrobial sacrificial floor coating composition is adapted to cure on a floor surface in about 30 to 60 minutes at a humidity ranging from 20% to 80% thereby forming a clear (e.g., transparent and/or translucent), thin film coating on the floor that exhibits continuous sanitization (i.e., antimicrobial properties) from full cure of the coating up to 6 months (or even up to 1 year) post-application on flooring surface having light, moderate, and heavy pedestrian traffic. In certain aspects, the antimicrobial sacrificial floor coating is adapted to exhibit a log reduction from 3.25 to 6, from 3.25 to 5, from 3.3 to 6, from 3.3 to 5, from 3.85 to 6, from 3.85 to 5.9, from 3.85 to 5.75, from 3.9 to 5.75, from 4.2 to 5.75, from 4.5 to 5.75, from 4.75 to 5.75, from 5 to 5.75, from 5.3 to 5.75, from 4.4 to 5.5, or from 4.6 to 4.9 for gram negative bacteria and/or a log reduction from 3.0 to 6.3, from 3.0 to 4.0, from 3.05 to 6.3, from 3.1 to 6.3, from 3.1 to 5, from 3.25 to 6.3, from 3.25 to 5.75, from 3.25 to 4.5, from 3.5 to 5.0, from 3.5 to 4.5, from 3.75 to 6.0, from 3.75 to 5.0, from 3.75 to 4.5, or from 4.0 to 6.0 for gram positive bacteria at 1 hour post application of a bacterial inoculum, 2 hours post application of a bacterial inoculum, 4 hours post application of a bacterial inoculum, 6 hours post application of a bacterial inoculum, and/or 24 hours post application of a bacterial inoculum to a floor surface having the antimicrobial sacrificial floor coating composition applied (cured) thereon and up to six months (or even up to 1 year) post application on flooring surfaces having light, moderate, or heavy pedestrian traffic at minimum contact time of one hour. In certain aspects, antimicrobial activity of the clear, thin film coating formed by the antimicrobial sacrificial floor coating composition post application to the floor is based on the resulting clear, thin film having a thickness ranging from 0.2 mils to 1.1 mils, more preferably from 0.25 to 0.7 mils, 0.2 mils to 1.1 mils, from 0.2 mils to 1.0 mils, from 0.25 mils to 0.9 mils, from 0.25 mils to 0.8 mils, from 0.3 mils to 0.5 mils, or from 0.3 mils to 0.4 mils. In certain aspects, the gram negative bacteria disclosed herein include at least *E. coli* (e.g., *Escherichia coli* ATCC 8739) and/or *P. aeruginosa* (e.g., *Pseudomonas aeruginosa* ATCC 15442), and in certain aspects, the gram positive bacteria disclosed herein include at least *S. aureus* (e.g. *Staphylococcus aureus* ATCC 6538).

Nonionic Acrylic Polymer of the Floor Coating

In most traditional floor coatings, anionic surfactants (e.g., anionic acrylates) are used to ensure emulsion stability during and after manufacturing at a surfactant load that does not compromise the durability and performance of the polymers in the coating formulation. However, unlike most traditional floor coatings, the disclosed antimicrobial sacrificial floor coating compositions utilize a nonionic acrylic polymer to ensure optimal efficacy of the antimicrobial agent(s) (e.g., a cationic alkyl biguanide or salt thereof) included in the disclosed antimicrobial sacrificial floor coating(s) while concurrently minimizing the likelihood of gradual viscosity increase(s), coagulation, and/or poor film formation. In addition to these benefits, including a nonionic acrylic polymer in the disclosed antimicrobial sacrificial floor coating compositions further prevents and/or reduces decreased glossiness and/or water resistance of these coatings post-application to a floor.

In certain aspects, the nonionic acrylic polymer includes, for example, acrylic emulsions such as a waterborne acrylic resin. The nonionic acrylic polymer may have a pH of between 3.5 to 4.5 and more preferably a pH of 3.8 to 4.3 before being included in the disclosed antimicrobial sacrificial floor coatings and may further include a minimum film forming temperature (MFFT) of at least 25° C., more preferably of at least 28° C., and most preferably of at least 30° C. In certain aspects, the nonionic acrylic polymer is a waterborne acrylic resin that includes methyl methacrylate. The molecular weight of the nonionic acrylic polymer is at least 460,000 as determined by gel permeation chromatography, and the nonionic acrylic polymer is present at a concentration ranging from 30 to 40 wt %, from 31.5 to 39 wt %, from 33 to 37.5 wt %, from 34 to 36 wt %, or from 35 to 36 wt % of the antimicrobial sacrificial floor coating compositions. A suitable nonionic acrylic polymer to be included in the disclosed antimicrobial sacrificial floor coating composition(s) is NeoCryl® XK-30 manufactured by DSM Coating Resins, LLC.

Nonionic Wax of the Floor Coating

In certain aspects, a nonionic wax is included in the disclosed antimicrobial sacrificial floor coating compositions to ensure chemical compatibility with the nonionic acrylic polymer and to further ensure optimal efficacy of the antimicrobial agent (e.g., a cationic alkyl biguanide or salt thereof).

The nonionic wax is a nonionic alkylene polymer including, for example, polyethylene or derivative thereof (e.g., oxidized polyethylene), polypropylene or a derivative thereof (e.g., oxidized polypropylene), or a combination thereof. The nonionic wax may more preferably include a high density polyethylene or derivative thereof (e.g., a nonionic oxidized high density polyethylene), high density polypropylene or derivative thereof (e.g., a nonionic oxidized high density polypropylene), or a combination thereof having a molecular weight from 8,000 to 20,000 g/mol, from 8,000 to 17,500 g/mol, from 8,000 to 15,000 g/mol, from 8,000 to 12,500 g/mol, from 8,000 to 10,000 g/mol, from 9,000 to 18,000 g/mol, from 9,000 to 14,000 g/mol, from 9,000 to 12,000 g/mol, from 9,000 to 11,500 g/mol, from 9,000 to 11,000 g/mol, from 9,000 to 10,500 g/mol, from 9,000 to 10,000 g/mol, or from 9,000 to 9,500 g/mol because these chemistries impart black mark, scuff mark, and mark resistance to the floor finish.

The nonionic wax may be present at a concentration ranging from 2 wt % to 12 wt %, more preferably 2.5 wt % to 8 wt %, and most preferably from 2.75 wt % to 4 wt % of the antimicrobial sacrificial floor coating composition. The nonionic wax most preferably is a high density polyethylene (e.g., a nonionic oxidized high density polyethylene) at a concentration of between 2 wt % to 12 wt %, more preferably 2.5 wt % to 8 wt %, and most preferably from 2.75 wt % to 4 wt % and has a molecular weight ranging between 9,000-10,000 g/mol. The above mentioned molecular weight and/or concentration endpoints are important to maintain adequate viscosity while imparting black mark resistance, scuff mark resistance, and mark resistance to the floor finish. If nonionic wax concentration falls below the lowest concentration and/or lowest molecular weight endpoints mentioned above, then undesirable loss in mar resistance occurs. Thus, including a nonionic wax at concentrations and/or molecular weights below those mentioned above should be avoided.

A suitable nonionic wax that can be included in the antimicrobial sacrificial floor coating composition is Aquacer 8030 and/or Aquacer 8059, each manufactured by BYK USA Inc. (CAS-Nos. 68131-39-5 and 61791-26-2 respectively).

Cationic Wax of the Floor Coating

Cationic wax is further included in the disclosed antimicrobial sacrificial floor coating compositions. Although antimicrobial sacrificial floor coating compositions may include a nonionic acrylic polymer, a nonionic wax, and an antimicrobial agent including cationic alkyl biguanide or salt thereof while omitting a cationic wax, it should be further noted that the antimicrobial sacrificial floor coating compositions omitting cationic wax may in some instances be susceptible to heat/temperature instability (e.g., increased viscosity—resulting in viscosities well above 10 cP, 100 cP, or 200 cP, decreased antimicrobial activity, etc.) especially when subjected to prolonged heat exposure including, for example, exposed to temperatures of 120° F. or more for up to 30 days. Thus, to ensure that the antimicrobial sacrificial floor coating compositions maintain adequate stability, viscosity, and/or mar resistance during prolonged heat exposure, a cationic wax is preferably included in the antimicrobial sacrificial floor coating compositions.

In certain aspects, the cationic wax is a cationic alkylene polymer and/or an emulsion including the cationic alkylene polymer. For example the cationic alkylene polymer may include cationic oxidized alkylene(s) and/or emulsions including cationic oxidized alkylene(s). The cationic alkylene polymer may specifically include high or low density oxidized polyethylene, high or low density oxidized polypropylene, or a combination thereof. In certain aspects, the cationic wax is an emulsion including high density oxidized polyethylene wax. The cationic wax (cationic alkylene polymer and/or an emulsion including the cationic alkylene polymer) preferably has a molecular weight ranging between 1,000 to 50,000 g/mol and more preferably between 5,000 to 15,000 g/mol because these chemistries impart black mark, scuff mark, and mark resistance to the floor finish.

In certain aspects, the cationic wax may include an emulsion of a cationic oxidized high density alkylene polymer, which includes, for example, a cationic oxidized high density polyethylene, a cationic oxidized high density polypropylene, or a combination thereof.

In certain aspects, the cationic wax may be present in the antimicrobial sacrificial floor coating composition at a concentration of between 2 wt % to 12 wt %, more preferably 2.5 wt % to 8 wt %, and most preferably from 2.75 wt % to 5.0 wt % of the antimicrobial sacrificial floor coating composition. For example, a cationic oxidized high density polyethylene, a cationic oxidized high density polypropylene, or a combination thereof may be used in the disclosed formulations having at a concentration between 2 wt % to 12 wt %, preferably 2.5 wt % to 8 wt %, and most preferably from 2.75 wt % to 5.0 wt % of the overall composition. In certain preferred aspects, the cationic wax is a cationic oxidized, high density polyethylene at a concentration of between 2.5 wt % to 8 wt % of the antimicrobial sacrificial floor coating composition and has a molecular weight ranging between 1,000 to 50,000 g/mol and more preferably between 5,000 to 15,000 g/mol. In certain aspects, the ratio of cationic wax to nonionic wax in the antimicrobial sacrificial floor coating ranges from 1.25:1 to 1:1.25, more preferably the ratio of cationic wax to nonionic wax in the antimicrobial sacrificial floor coating is 1:1.

A suitable cationic wax that can be included in the antimicrobial sacrificial floor coating composition is Aquacer 840 manufactured by BYK USA Inc. (CAS-No. 61791-26-2).

Antimicrobial Agent of the Floor Coating

The antimicrobial sacrificial floor coating compositions further include an antimicrobial agent to control, reduce, and/or prevent growth of gram positive and/or gram negative bacteria. In particular, the antimicrobial agent includes a cationic alkyl biguanide or salt thereof because of its charge, antimicrobial efficacy over extended periods of time, and compatibility with the disclosed nonionic acrylic polymer, nonionic wax, and cationic wax. For example, the antimicrobial agent preferably includes a cationic alkyl biguanide.

The cationic alkyl biguanides include at least one or more biguanide moiety according to the following formula:

In the context of the compositions of this invention, the cationic alkyl biguanide is a cationic oligo- or poly alkylene biguanide(s) or salts thereof or mixtures thereof.

In a most preferred embodiment, the cationic alkyl biguanide is a poly (hexamethylene biguanide) or salt thereof according to the following formula:

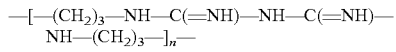

wherein n is an integer selected from about 1 to about 50, preferably about 1 to about 20, more preferably about 9 to about 18, most preferably 12 to 15.

More preferably said biguanide antimicrobial agents is a salt of a poly (hexamethylene biguanide) according to the following formula:

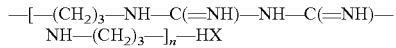

wherein n is an integer selected from about 1 to about 50, preferably about 1 to about 20, more preferably about 9 to about 18, most preferably 11 to 15, and HX is salt component, preferably HCl.

A most preferred cationic alkyl biguanide is poly (hexamethylene biguanide) hydrochloride (PHMB), wherein in the above formula n=12 having a molecular weight of 2850 and is commercially available under the trade name Vantocil™ P Antimicrobial (EPA Registration No.: 1258-1252) from Lonza. The choice of poly (hexamethylene biguanide) hydrochloride, as the most preferred polymeric biguanide antimicrobial for the compositions of this invention is driven by its unusually good filming and streaking properties within the scope of the compositions disclosed herein, and by its regulatory status as an approved antimicrobial active for hard surface cleaning applications in the United States. In certain aspects, polyaminopropyl biguanide (PAPB) may also be included with PHMB to further increase antimicrobial efficacy.

Typically the compositions herein may comprise up to about 5 wt %, preferably from about 0.01% to about 4.5 wt %, more preferably from about 0.02% to about 4.0 wt %, by weight of the total composition of the cationic alkyl biguanide. At the active use levels, following recommended product dilution, if any, the compositions herein may comprise up to about 1 wt %, preferably from about 0.01% to about 1.0 wt %, more preferably from about 0.3% to about 1.0 wt %, more preferably from about 0.4% to 1.0 wt %, more preferably from about 0.45% to 0.95 wt %, even more preferably from about 0.5 to 0.95 active wt %, more preferably from about 0.6 to 0.95 active wt %, even more preferably from about 0.65 to 0.95 active wt %, and most preferably from 0.74 to 0.95 active wt % by weight of the total composition of the cationic alkyl biguanide for extend periods of effectiveness against gram positive and gram negative bacteria. The weight percentage of the cationic alkyl biguanide disclosed herein preferably refers to the concentration of the active amount of cationic alkyl biguanide in the disclosed compositions.

Additives/Diluents of the Floor Coating

In certain aspects, the disclosed compositions include additional additives and preservatives, including, for example, wetting agents, leveling agents, and other chemical components for aiding in extending shelf life of the composition and/or for aiding in desired film formation during application of the composition to a floor. For example, various siloxanes at concentrations ranging from 0.5 wt % to 5 wt %, from 0.7 wt % to 4 wt %, or from 0.8 wt % to 3 wt % of the antimicrobial sacrificial floor coating composition may be used in the disclosed compositions as wetting agents and/or leveling agents. These siloxanes more specifically may include a polyether modified siloxane at a concentration from 0.8 wt % to 1.3 wt % of the antimicrobial sacrificial floor coating composition, and more preferably at a concentration of 0.9-1.0% wt of the total composition to ensure proper flooring substrate wetting and leveling, without causing foam formation. In certain aspects, the polyether modified siloxane is a fluorine free, polydimethylsiloxane at a concentration of 0.8 wt % to 1.2 wt % of the total composition, and most preferably at a concentration of 0.9-1.0 wt % of the total composition. Examples of polyether modified siloxanes include Byk®-3455. Also, as alluded to above, the disclosed compositions may further include additional chemical components that aid in coalescing the disclosed compositions, as well as film formation. For example, in certain aspects, coalescing solvents such as a hydrophobic glycol ether(s) may be used in the disclosed compositions at concentrations ranging from 1 wt % to 10 wt %, from 1.5 wt % to 8 wt %, from 2.0 wt % to 7 wt % from 2.0 wt % to 5 wt % of the overall composition to obtain the desired coalescing and film forming properties. Examples of hydrophobic glycol ether include alkyl glycol alkyl ethers such as tripropylene glycol n-butyl ether, propylene glycol phenyl ether, tripropylene glycol methyl ether, propylene glycol n-butyl ether, ethylene glycol phenyl ether, and dipropylene glycol n-propyl ether. In preferred aspects, the disclosed composition at least includes tripropylene glycol n-butyl ether at a concentration ranging from 2.0 wt % to 3.0 wt % of the overall composition to impart desired coalescing and film formation properties. Preservatives that aid in providing long-term composition stability may be further provided at concentrations ranging from 0.01 wt % to 0.1 wt %, from 0.03 wt % to 0.09 wt %, from 0.04 wt % to 0.08 wt % of the coating composition. Examples of the preservatives used in the coating composition includes Acticide® CBM 2 (i.e., a mixture of 5-chloro-2-methyl-4-isothiazolin-3-one (1%) and 2-methyl-4-isothiazolin-3-one (5%) and 1,2-benzisothiazolin-3-one (10%); EPA Registration No. 67071-62) at a concentration ranging from 0.01 wt % to 0.1 wt %, from 0.03 wt % to 0.09 wt %, from 0.04 wt % to 0.08 wt % of the coating composition. In certain aspects, water is included in the antimicrobial sacrificial floor coating compositions at a concentration ranging from 30 to 65 wt %, from 37.5 to 62.5 wt %, from 40 to 60 wt %, from 42.5 to 57.5 wt %, from 45 to 55 wt %, from 45 to 52.5 wt %, or from 45 to 50 wt % of the antimicrobial sacrificial floor coating composition.

pH and Viscosity of the Floor Coating

The disclosed antimicrobial sacrificial floor coating compositions have a pH of about 7 or less, which improves storage stability and antimicrobial agent (e.g., cationic alkyl biguanide) efficacy. It is found that at a pH higher than about 7 storage instability increases while efficacy of the antimicrobial agent (e.g., cationic alkyl biguanide) decreases. Thus, for at least these reasons, the pH range of the antimicrobial sacrificial floor coating compositions is preferably a pH from about 0.5 to about 7, more preferably a pH from about 1 to 6, even more preferably a pH from about 3 to 5.5, and most preferably a pH from about 4 to 5. The disclosed antimicrobial sacrificial floor coatings further have a viscosity ranging from 1 cP to 10 cP, preferably from 2.5 cP to 8 cP, and most preferably from 4 to 6 cP. As disclosed herein, the antimicrobial sacrificial floor coatings maintain the above discussed viscosities even when subjected to high temperatures for prolonged periods of time (e.g., 120° F. for up to 30 continuous days).

Method(s) of Making the Floor Coating

In certain aspect, also disclosed are methods of making the antimicrobial sacrificial floor coating compositions. The antimicrobial sacrificial floor coating compositions may be emulsions in which the nonionic acrylic polymer is admixed with the nonionic wax, cationic wax, antimicrobial agent and coalescing solvent thereby forming the antimicrobial sacrificial floor coating composition. The nonionic acrylic polymer is preferably admixed with the coalescing solvent, nonionic wax, cationic wax, and antimicrobial agent for a sufficient time period such that each component is homogeneously dispersed throughout the antimicrobial sacrificial floor coating compositions and no precipitate(s) are visibly observable. Homogeneous dispersion of the chemical components in the antimicrobial sacrificial floor coating composition further ensures that a clear film will form having sufficient and even thickness (e.g., from 0.2 mils to 1.1 mils, more preferably from 0.25 mils to 0.7 mils, 0.2 mils to 1.1 mils, from 0.2 mils to 1.0 mils, from 0.25 mils to 0.9 mils, from 0.25 mils to 0.8 mils, from 0.3 mils to 0.5 mils, or from 0.3 mils to 0.4 mils in thickness) post application to the floor.

Methods of Applying the Antimicrobial Sacrificial Floor Coating

The disclosed antimicrobial sacrificial floor coating compositions may be applied to floors via synthetic or cotton string mop or microfiber flat mop. Specific flooring surfaces to which these compositions may be applied include, for example, wood floors, vinyl floors, ceramic floors, natural stone floors, terrazzo floors, cement floors, or other types of polymeric composite floors. In certain aspects, the disclosed antimicrobial sacrificial floor coating compositions are applied to floors having a conventional floor finish as further discussed below in the Working Examples.

Post application to the floor, these compositions form a clear, thin film coating having a film-forming temperature ranging between 0 to 90° C., 10 to 80° C., or 15 to 50° C. When applied to the floor, these compositions exhibit a log reduction from 3.3 to 5.75 for gram negative bacteria and a log reduction from 3.11 to 6.3 for gram positive bacteria at 1 hour post application, 2 hours post application, 4 hours post application, 6 hours post application and 24 hours post application to a floor surface. In certain aspects, antimicrobial activity of the clear, thin film coating formed by the antimicrobial sacrificial floor coating composition post application to the floor is based on the resulting clear, thin film having a thickness ranging from 0.2 mils to 1.1 mils, more preferably from 0.25 mils to 0.7 mils.

Post-application to the floor, these compositions begin reducing growth and/or preventing growth of gram positive and gram negative bacteria almost immediately and exhibit antimicrobial efficacy/growth inhibitory activity for extended periods of time. For example, in certain aspects, the disclosed antimicrobial sacrificial floor coating compositions exhibit antimicrobial efficacy for at least one month, preferably for at least two months, more preferably for at least three months, more preferably for at least four months, even more preferably for at least six months, and most preferably for up to 1 year post-application to a floor. In certain aspects, these compositions preferably reduce and/or prevent *Escherichia coli, Pseudomonas aeruginosa*, and *Staphylococcus aureus* growth for at least between 30 to 90 days and more preferably up to 180 days (i.e., up to 6 months or even up to 1 year).

Antimicrobial Sacrificial Floor Coating Remover

As alluded to above, the antimicrobial sacrificial floor coating may be periodically removed from and reapplied to flooring surfaces as desired by a user of the system. Thus, disclosed is a solution (antimicrobial sacrificial floor coating remover) for efficiently removing the antimicrobial sacrificial floor coating from flooring surfaces as desired by the user (e.g., at least once a month, once every 2 months, once every 3 months, or once every 4 months, 5 months, or 6 months).

Unlike most conventional stripping solutions, the disclosed antimicrobial sacrificial floor coating remover is an acidic solution that does not remove the antimicrobial sacrificial floor coating via an emulsification process (e.g., re-liquefying), but instead, intercalates and swells the antimicrobial sacrificial floor coating thereby making the swollen coating susceptible to and/or allowing for mechanical removal (e.g., via scrubbing and/or brushing) of the antimicrobial sacrificial floor coating from the flooring surface. Also, unlike most conventional stripping solutions, the disclosed antimicrobial sacrificial floor coating remover includes little and/or preferably no volatile organic compounds (VOCs).

In certain aspects, the antimicrobial sacrificial floor coating remover includes (a) an organic solvent at a concentration ranging from 17 wt % to 30 wt % of the antimicrobial sacrificial floor coating remover; (b) a nonionic surfactant at an effective concentration for aiding in wetting and increasing water solubility of the organic solvent in the antimicrobial sacrificial floor coating remover; and (c) an organic acid at a concentration ranging from 1 wt % to 5 wt % of the antimicrobial sacrificial floor coating remover. The antimicrobial sacrificial floor coating remover preferably further includes water ranging from 60 wt % to 80 wt %, more preferably from 65 wt % to 77.5 wt %, and most preferably from 72 wt % to 76 wt % of the antimicrobial sacrificial floor coating remover. The individual components of the antimicrobial sacrificial floor coating remover and the advantageous properties that each component imparts are discussed in greater detail below. As also discussed further below, the antimicrobial sacrificial floor coating remover may be a concentrated solution configured for dilution to remove the antimicrobial sacrificial floor coating(s) from floor(s). The concentrated solution has a pH ranging from 2.0 to 3.0, and more preferably from pH 2.35 to 2.7. When water is present in the concentrated solution, the overall actives (i.e., organic solvent, nonionic surfactant, and organic acid) are present from 20 to 30 wt %, more preferably from 22 to 27.5 wt %, and most preferably from 24 to 26.5 wt % of the overall concentrated remover while water is present from 70 to 80 wt %, more preferably from 72.5 to 78 wt %, and most preferably from 73.5 to 76 wt % of the overall concentrated remover.

Organic Solvent

As alluded to above, the antimicrobial sacrificial floor coating remover includes an organic solvent at a concentration effective to disrupt the antimicrobial sacrificial floor coating. The organic solvent is included in the antimicrobial sacrificial floor coating remover at a concentration ranging from 17 wt % to 30 wt %, more preferably from 19 wt % to 27 wt %, and most preferably from 22 wt % to 24 wt %. Although the remover may include only one organic solvent, in certain aspects, the remover includes a two organic solvent system in which each organic solvent synergistically interacts with one another to more effectively disrupt the antimicrobial sacrificial floor coating when compared to only including a single organic solvent in the remover.

In certain aspects, the first organic solvent included in the antimicrobial sacrificial floor coating remover is a glycol ether or a derivative thereof at a concentration ranging from 16 to 25 wt %, more preferably from 17 wt % to 23 wt %, and most preferably from 18 wt % to 21 wt % of the antimicrobial sacrificial floor coating remover. The glycol ether or derivative thereof preferably is selected from diethylene glycol monobutyl ether, ethylene glycol monomethyl ether, ethylene glycol monoethyl ether, ethylene glycol monopropyl ether, ethylene glycol monoisopropyl ether, ethylene glycol monobutyl ether, diethylene glycol monomethyl ether, and/or diethylene glycol monoethyl ether. In certain aspects, the above mentioned glycol ethers are preferred because these glycol ethers have higher boiling points than lower-molecular weight ethers and alcohols but maintain favorable solvent properties similar to lower-molecular weight ethers. Thus, the glycol ethers of the first organic solvent are stable at ambient conditions and do not readily evaporate from the antimicrobial sacrificial floor coating remover, thus providing greater stability and longer lifespan (shelf life) to the remover. In certain aspects, diethylene glycol monobutyl ether (e.g., Eastman™ DB Solvent CAS No. 112-34-5) is particularly preferred as the first organic solvent in the antimicrobial sacrificial floor coating remover at a concentration ranging from 18-21 wt % because concentrations either higher or lower do not provide adequate balance of efficient coating removal and/or machine pad load.

In certain aspects, the second organic solvent of the remover is present at a concentration lower than the first organic solvent. The second organic solvent preferably has high solvent activity while preferably having no or lower vapor pressure VOC emissions. For example, the second organic solvent may be present in the remover at a concentration ranging from 1 to 7 wt %, 1.5 to 6 wt %, more preferably from 2 to 5 wt %, or most preferably from 2.5 to 3.5 wt % of the remover. In certain aspects, the second organic solvent is a conjugate base of an organic acid including, for example, propionate or derivatives thereof, butanoate or derivatives thereof, or pentanoate or derivatives thereof. Particularly preferred are butanoate or derivatives thereof including butan-1-yl-3-hydroxybutanoate (e.g., Eastman Omnia™ CAS Number: 53605-94-0) at a concentration ranging from 2 to 5 wt % or most preferably from 2.5 to 3.5 wt % of the remover.

Regarding the above mentioned two organic solvent system, in certain aspects, it is preferred to include diethylene glycol monobutyl ether as the first organic solvent in the antimicrobial sacrificial floor coating remover at a concentration ranging from 19 wt % to 21 wt % of the remover and butan-1-yl-3-hydroxybutanoate as the second solvent in the remover at a concentration ranging from 2.5 to 3.5 wt % of the remover because these two solvents cooperatively and synergistically interact to disrupt the antimicrobial sacrificial floor coatings disclosed herein than when solely using either solvent alone in a remover.

Nonionic Surfactant

The antimicrobial sacrificial floor coating removers further include at least one nonionic surfactant that preferably has excellent wetting and/or degreasing properties, while also concurrently chemically interacting with and increasing water solubility of the organic solvent(s) present in the remover. The nonionic surfactant is present at a concentration ranging from 0.2 to 3 wt %, from 0.3 to 2.5 wt %, from 0.4 to 2.0 wt %, from 0.45 to 1.75 wt %, or from 0.5 to 1.5 wt % of the remover. Examples of nonionic surfactants include ethoxylated alcohols, carboxylic esters, and/or polyethylene glycol esters.

In preferred aspects, the nonionic surfactant includes an ethoxylated alcohol that is more specifically a linear alcohol ethoxylate having the following formula:

$RO(CH_2CH_2O)_nH$ wherein R is a linear primary alcohol and n is the total number of moles of ethylene oxide. For example, R includes a linear C9-C15 primary alcohol and is preferably a C9-C11 primary alcohol while n is either 2.5, 6, or 8. In certain aspects, R is preferably a C9-C11 primary alcohol while n is 6. The above mentioned ethoxylated alcohol(s) further includes a hydrophilic-lipophilic balance (HLB) value of from 8.5 to 14, preferably ranging from 12.2 to 12.6. A suitable ethoxylated alcohol can include, for example, Tomdol® 91-6. The above mentioned ethoxylated alcohols are particularly preferred, especially $RO(CH_2CH_2O)_nH$ wherein R is a C9-C11 primary alcohol and n is 6, because of their excellent wetting and/or degreasing properties, while concurrently increasing water solubility of the disclosed organic solvent(s) in the remover thereby increasing stability and effectiveness of the remover.

Organic Acid

The antimicrobial sacrificial floor coating remover according to the invention further includes at least one organic acid. Organic acids are preferred over inorganic acids because organic acids are not as harsh and/or corrosive as inorganic acids. The disclosed organic acids further advantageously chemically interact with the organic solvent and nonionic surfactant to provide a stable antimicrobial sacrificial flooring coating remover (removing solution) to effectively intercalate and/or swell the antimicrobial sacrificial flooring coating for subsequent removal of the coating as described further herein. In contrast to the disclosed organic acids and as further evidence in the Working Examples, antimicrobial sacrificial floor coating remover(s) of the invention (also termed remover(s) in the present text) including inorganic acids were partially or completely ineffective for removing the disclosed antimicrobial sacrificial floor coatings.

In certain aspects, the organic acid is included in the remover at a concentration ranging from 1 to 7 wt %, from 1 to 5 wt %, from 1 to 4 wt %, from 1 to 2.5 wt %, or from 1.2 to 1.9 wt % of the antimicrobial sacrificial floor coating remover. The organic acid preferably includes a carboxylic acid moiety (—COOH) and has a pKa ranging from 3.8 to 4.9. In certain aspects, the carboxylic acid moiety is R—COOH wherein R is a linear or branched C1-C6 alkyl, a C1-C6 primary alcohol, or a C1-C6 secondary alcohol, For example, the organic acid may include at least one of the following: formic acid, acetic acid, propanoic acid or derivatives thereof (e.g., lactic acid-2 hydroxypropanoic acid), butyric acid or derivatives thereof, valeric acid or derivatives thereof, or caproic acid. In preferred aspects, the organic acid is lactic acid because of its compatibility with the disclosed organic solvent(s) (e.g., increases solubility of the organic solvent(s) in the remover) and because of its favorable human health profile. The lactic acid may be L-lactic acid, D-lactic acid, or racemic mixtures thereof at a concentration ranging from 1 to 7 wt %, from 1 to 5 wt %, from 1 to 4 wt %, from 1 to 2.5 wt %, or from 1.2 to 1.9 wt % of the remover. In certain aspects, the organic acid is L-lactic acid being at least 80%, 85%, 87.5%, 90%, 95%, 98%, 99%, or 99.9% pure at a concentration ranging from 1 to 7 wt %, from 1 to 5 wt %, from 1 to 4 wt %, from 1 to 2.5 wt %, or from 1.2 to 1.9 wt % of the remover.

Dilution and Method(s) of Applying Antimicrobial Sacrificial Floor Coating Remover In certain aspects, the above disclosed antimicrobial sacrificial floor coating remover is a concentrate/concentrated solution having an initial pH ranging from 2.0 to 3.0, more preferably 2.35 to 2.8. The concentrated solution preferably includes actives (i.e., organic solvent, nonionic surfactant, and organic acid) ranging from 20 to 30 wt %, more preferably from 22 to 27.5 wt %, and most preferably from 24 to 26.5 wt % of the overall remover while water is present from 70 to 80 wt %, more preferably from 72.5 to 78 wt %, and most preferably from 73.5 to 76 wt % of the overall remover.

To obtain a working concentration of the antimicrobial sacrificial floor coating remover having the preferred dwell time (e.g., between 5 to 10 minutes) to intercalate, swell, and subsequently remove the antimicrobial sacrificial coating from the floor, the concentrated solution is first diluted with water and mixed to obtain a homogenous mixture. For example, the dilution may include 1 part concentrated remover to 6 parts water (1:6 dilution), 1 part concentrated remover to 5 parts water (1:5 dilution), 1 part concentrated remover to 4 parts water (1:4 dilution) thereby forming a working concentration of the antimicrobial sacrificial floor coating remover. The antimicrobial sacrificial floor coating remover also preferably has high buffering capacity allowing the initial pH to be maintained during and after dilution with water. For example, after diluting the antimicrobial sacrificial floor coating remover as discussed immediately above, pH of the working solution ranges from pH 2.0 to 3.0, more preferably from pH 2.35 to 2.8, or most preferably from pH 2.6 to 2.8. In certain aspects, a 1:5 dilution is preferred because it provides optimum solvency and acid content to attack the antimicrobial sacrificial floor coating, while including enough water to slow down evaporation during dwell time and suspend the antimicrobial sacrificial floor coating during mechanical removal.

After diluting the concentrated remover (e.g., with a 1:5 dilution of concentrated remover to water), the diluted remover is applied to a flooring surface that was previously treated with the antimicrobial sacrificial floor coating. For example, in certain preferred aspects, the antimicrobial sacrificial floor coating (having the thicknesses and antimicrobial properties disclosed herein) had been previously applied to the floor one month, two months, three months, six months, or up to one year prior to removal. In this example, the diluted remover (working solution) is applied to the floor via mopping at a rate of approximately 100 sq ft/diluted gallon or diluted remover. After applying the diluted remover to the flooring surface previously treated with the antimicrobial sacrificial floor coating, the diluted remover is allowed to rest/dwell for a predetermined timer period to intercalate and/or swell the antimicrobial sacrificial floor coating. For example, in certain preferred aspects, dwell time ranges from 3 to 12 minutes and more preferably from 5 to 10 minutes. After allowing for adequate dwell time, the antimicrobial sacrificial floor coating swells/is disrupted by the remover and is susceptible to mechanical/physical removal via, for example, scrubbing, brushing, and/or a low speed floor machine. In preferred aspects, the antimicrobial sacrificial floor coating has been completely removed by one application of the remover and subsequent application of mechanical/physical force. However, if any residual antimicrobial sacrificial floor coating remains on the floor and/or if desired by the user, the diluted remover may again be re-applied and the steps discussed immediately above may be repeated to further remove any residual antimicrobial sacrificial floor coating.

Following removal of the antimicrobial sacrificial floor coating, a new antimicrobial sacrificial floor coating using the formulation disclosed herein may be re-applied. Alternatively and if a conventional floor finish (e.g., zinc cross-linked floor finish) was below the antimicrobial sacrificial floor coating, a conventional floor stripper may then be applied to strip the conventional floor finish. After stripping the conventional floor finish, the conventional floor finish may be re-applied to the floor and allowed to dry. After drying, the antimicrobial sacrificial floor coating may be applied over the conventional floor finish and allowed to dry thereby providing the antimicrobial characteristics to the floor as described herein.

Antimicrobial Sacrificial Floor System Kit

The above disclosed antimicrobial sacrificial floor coating compositions and the above disclosed antimicrobial sacrificial floor coating remover(s) may be packaged into a kit. Particularly in certain aspects, the kit includes the antimicrobial sacrificial floor coating composition according to the invention in a first container and further includes the antimicrobial sacrificial floor coating remover according to the invention in a second container. The antimicrobial sacrificial floor coating compositions and antimicrobial sacrificial floor coating remover(s) are used as described herein.

WORKING EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric.

Antimicrobial Sacrificial Floor Coating Composition

Shown below in Tables 1 and 2 are exemplary antimicrobial sacrificial floor coating compositions made with the chemical components and methods disclosed herein. Also shown below in Tables 3 and 4 are two comparative formulations (i.e., Comparative Example 1 and Comparative Example 2).

Comparative Example 1 has the same active ingredient as the Exemplary Antimicrobial Sacrificial Floor Coating Composition in Tables 1 and 2, but includes a standard anionic floor finish polymer system instead of the nonionic polymer system utilized by Exemplary Antimicrobial Sacrificial Floor Coating Composition of Tables 1 and 2. With regard to Comparative Example 1, it should be further noted that coagulation occurred and was immediately visible after adding the PHMB, leading PHMB to settle out of solution quickly. The coating of Comparative Example 1 was unable to be applied to a substrate and/or tested for antimicrobial efficacy due to the adverse cationic/anionic reaction of the PHMB and acrylic polymer.

Like Comparative Example 1, Comparative Example 2 also utilized a standard anionic floor finish polymer system, but instead of including PHMB, Comparative Example 2 included an anionic antimicrobial agent, sodium omadine, which is compatible with anionic polymers. These compositions were tested as discussed further below, but Comparative Example 2 showed no log reduction at 2 and 6 hours respectively post-application to a substrate.

TABLE 1

First Exemplary Antimicrobial Sacrificial Floor Coating Composition

| Component | wt % |
|---|---|
| Water | 48.252 |
| Nonionic Acrylic Emulsion[2] | 35.922 |
| Nonionic Oxidized High Density Polyethylene Emulsion[3] | 9.709 |
| Poly (Hexamethylene Biguanide) Hydrochloride[4] | 2.913[1] |
| Tripropylene Glycol n-Butyl Ether | 2.233 |
| Polyether Modified Siloxane[5] | 0.971 |

[1]The active content/concentration of Poly (Hexamethylene Biguanide) Hydrochloride was 0.5826 wt % because the Poly (Hexamethylene Biguanide) Hydrochloride added to solution included 80% non-active Poly (Hexamethylene Biguanide) Hydrochloride (e.g., fillers, etc.). Thus, 0.2 (i.e., 20%) × 2.913 = 0.5826 wt %.
[2]The Nonionic Acrylic Emulsion used was NeoCryl® XK-30 manufactured by DSM Coating Resins, LLC.
[3]The Nonionic Oxidized High Density Polyethylene Emulsion used was Aquacer 8030 manufactured by BYK USA Inc. (CAS-No. 68131-39-5).
[4]The Poly (Hexamethylene Biguanide) Hydrochloride used was Vantocil™ P Antimicrobial (EPA Registration No.: 1258-1252) from Lonza.
[5]The Polyether Modified Siloxane used was BYK 3455 manufactured by BYK USA Inc.

TABLE 2

Second Exemplary Antimicrobial Sacrificial Floor Coating Composition

| Component | wt % |
|---|---|
| Water | 50.048 |
| Nonionic Acrylic Emulsion[2] | 35.577 |
| Nonionic Oxidized High Density Polyethylene Emulsion[3] | 3.365 |
| Cationic Oxidized High Density Polyethylene Emulsion[4] | 3.942 |
| Poly (Hexamethylene Biguanide) Hydrochloride[5] | 3.846[1] |
| Tripropylene Glycol n-Butyl Ether | 2.212 |
| Polyether Modified Siloxane[6] | 0.962 |
| Acticide® CBM2 (Preservative)[7] | 0.048 |

[1]The active content/concentration of Poly (Hexamethylene Biguanide) Hydrochloride was 0.7692 wt % because the Poly (Hexamethylene Biguanide) Hydrochloride added to solution included 80% non-active Poly (Hexamethylene Biguanide) Hydrochloride (e.g., fillers, etc.). Thus, 0.2 (i.e., 20%) × 3.846 = 0.7692 wt %.
[2]The Nonionic Acrylic Emulsion used was NeoCryl® XK-30 manufactured by DSM Coating Resins, LLC.
[3]The Nonionic Oxidized High Density Polyethylene Emulsion used was Aquacer 8059 manufactured by BYK USA Inc. (CAS-No. 61791-26-2).
[4]The Cationic High Density Polyethylene Emulsion used was Aquacer 840 manufactured by BYK USA Inc. (CAS-No. 61791-26-2).
[5]The Poly (Hexamethylene Biguanide) Hydrochloride used was Vantocil™ P Antimicrobial (EPA Registration No.: 1258-1252) from Lonza.
[6]The Polyether Modified Siloxane used was BYK 3455 manufactured by BYK USA Inc.
[7]Acticide® CBM 2 manufactured by Thor Specialties Inc. (EPA Registration No. 67071-62).

TABLE 3

Antimicrobial Test Coating with Anionic Polymer
and Cationic PHMB (Comparative Example 1)

| Component | wt % |
|---|---|
| Water | 44.391 |
| Anionic Acrylic Polymer | 38.300 |
| Oxidized Polyethylene | 3.853 |
| Styrene/acrylic Copolymer | 3.468 |
| Diethylene Glycol Monoethyl Ether | 4.662 |
| Tributoxyethyl Phosphate | 2.485 |
| Anionic Olefin/Acrylate Graft Polymer Emulsion | 1.387 |
| Poly (Hexamethylene Biguanide) Hydrochloride | 1.000 |
| Dipropylene Glycol Monopropyl Ether | 0.405 |
| Isothiazolin | 0.025 |
| Anionic Fluorosurfactant | 0.015 |
| Silicone Emulsion | 0.010 |

TABLE 4

Antimicrobial Test Coating with Sodium
Omadine (Comparative Example 2)

| Component | wt % |
|---|---|
| Water | 43.853 |
| Anionic Acrylic Polymer | 37.836 |
| Oxidized Polyethylene | 3.806 |
| Styrene/acrylic Copolymer | 3.426 |
| Diethylene Glycol Monoethyl Ether | 4.605 |
| Tributoxyethyl Phosphate | 2.455 |
| Anionic Olefin/Acrylate Graft Polymer Emulsion | 1.370 |
| Triethanol amine | 0.900 |
| Dipropylene Glycol Monopropyl Ether | 0.400 |
| Isothiazolin | 0.024 |
| Sodium Omadine | 1.300 |
| Anionic Fluorosurfactant | 0.015 |
| Silicone Emulsion | 0.010 |

Antimicrobial efficacy of the formulations disclosed in Tables 1 and 4 were further tested using the below mentioned "Application" procedures and JIS Z2801 Bacterial Challenge. It should be noted that Comparative Example 1 in Table 3 was unable to be applied to a substrate and/or tested for antimicrobial efficacy because of this formulation's consistency, which was likely attributed to the adverse cationic/anionic reaction of the PHMB and acrylic polymer.

Application

A—Bench Testing

For the antimicrobial efficacy test(s), 3 coats of a 25% nonvolatile solids, conventional, floor finish were initially applied at a rate of 2000-3000 sqft/gal with cheesecloth. Next, the antimicrobial sacrificial floor finish (e.g., the formulation of Table 1) or the formulation in Table 4 (i.e., Comparative Example 2) was applied after the final coat of conventional floor finish with a 2" high density foam brush at roughly 4-13 grams per square foot and allowed to dry.

B—Floor Application

Three coats of a 25% nonvolatile solids, conventional, floor finish were applied to a stripped VCT floor at a rate of 2000-3000 sqft/gal with a microfiber floor finish flat mop. Next, the antimicrobial sacrificial floor finish (e.g., the formulation of Table 1) or the formulation in Table 4 (i.e., Comparative Example 2) was applied after the final coat of conventional floor finish with a microfiber floor finish flat mop at 1000-1100 sqft/gal and allowed to dry.

Test Results

Testing was conducted according to the JIS Z2801 Bacterial Challenge. Specifically, the formulation of Table 1 and a control were applied to separate (but identical) floor surface(s)/substrate(s) and allowed to dry (cure) thereby forming a film having approximately 0.33 mils thickness on the outermost surface of the floor surface/substrate. The control was identical to the formulation shown in Table 1 but excluded PHMB (i.e., the antimicrobial active agent). Each floor surface/substrate had an initial bacteria concentration of $8.2 \times 10^4$ CFU/sample *E. coli* ATCC 8739 (gram negative bacteria) and $6.1 \times 10^4$ CFU/sample *S. aureus* ATCC 6538 (gram positive bacteria) (inoculum) introduced onto the treated surface(s)/substrates (i.e., treated with the formulation of Table 1 or treated with the control) and bacterial log reductions were measured at 2, 6, and 24 hour increments during the JIS Z2801 Bacterial Challenge.

On the substrates treated with the formulation of Table 1, a 4.36 log reduction was observed for *E. coli* at 2 hours post-application of the inoculum to the treated substrate, a 4.44 log reduction was observed for *E. coli* at 6 hours post-application of the inoculum to the treated substrate; and a 5.40 log reduction was observed for *E. coli* at 24 hours post-application of the inoculum to the treated substrate. In addition to the log reduction observed for gram negative bacteria, gram positive bacteria log reductions were concurrently observed on the same substrates. For example, a 4.50 log reduction was observed for *S. aureus* (gram positive bacteria) at 2 hours post-application of the inoculum to the treated substrate; a 5.47 log reduction was observed for *S. aureus* at 6 hours post-application of the inoculum to the treated substrate; and a 6.26 log reduction was observed for *S. aureus* at 24 hours post-application of the inoculum to the treated substrate. Bacterial viability for the above discussed substrate(s) treated with the formulation of Table 1 was as follows: *E. coli* was $1.3 \times 10^1$ CFU for 2 hours, $3.4 \times 10^1$ CFU for 6 hours, and $6.3 \times 10^1$ CFU 24 hours post-application of the inoculum to the treated substrate, and *S. aureus* was $1 \times 10^1$ CFU for 2 hours, at 6 hours, and 24 hours post-application of the inoculum to the treated substrate.

The substrates treated with the control demonstrated no bacterial log reductions. Instead and as expected, bacterial CFUs increased. Bacterial viability of the substrate treated with the control was as follows: *E. coli* was $3.1 \times 10^5$ CFU at 2 hours post-application, $9.4 \times 10^6$ CFU at 6 hours post-application, and $1.6 \times 10^7$ CFU at 24 hours post-application, and *S. aureus* was $3.1 \times 10^5$ CFU at 2 hours post-application, $2.9 \times 10^6$ CFU at 6 hours post-application, and $1.8 \times 10^7$ CFU at 24 hours post-application of the inoculum to the floor surface treated with the control.

The substrate treated with the formulation of Table 1 was further subjected to detergent scrub resistance testing to determine the formulation's resistance to friction and durability while concurrently retaining antimicrobial efficacy. To test detergent scrub resistance, the Gardner scrub test was used, which included brushing/stroking the substrate with an unweighted hog bristle brush with a neutral pH, alkyl dimethyl benzyl ammonium chloride detergent cleaner for 100 cycles at 25 cycles/minute. During the Gardner scrub test, 100 strokes with the detergent represented 100 cleaning cycles. During the course of the Gardner scrub test, the antimicrobial efficacy of 3.85, 5.75, and 4.2 log reduction for *E. Coli* at 2, 6, and 24 hours and 4.27, 5.47, and 4.69 log reduction for *S. aureus* at 2, 6, and 24 hours remained stable while the comparative example(s) exhibited a zero log reduction when scrubbed. Bacterial viability of the substrate treated with the formulations of Table 1 subjected to scrub testing was as follows: *E. coli* concentration was $4.3 \times 10^1$ at 2 hours post-application, $1.7 \times 10^1$ at 6 hours post-application, and $9.8 \times 10^2$ at 24 hours post-application, and *S. aureus* was $1.7 \times 10^1$ at 2 hours, $1.0 \times 10^1$ at 6 hours, and $3.7 \times 10^2$ at 24 hours post-application. These results demonstrated that the antimicrobial agent was stably bound in the film (formed by the formulation of Table 1), was durable, and maintained antimicrobial efficacy while subjected to frictional force(s) for extended periods of time.

Instead of testing antimicrobial efficacy using the JIS Z2801 Bacterial Challenge, substrates were treated with the formulation of Table 2 or a control formulation (identical to the formulation of Table 2 but excluding PHMB) and were tested according to the EPA's Copper Method (i.e., proposed "Protocol for the Evaluation of Bactericidal Activity of Hard, Non-porous Copper Containing Surface Products"— awaiting final approval as of Apr. 22, 2017). See https://www.epa.gov/sites/production/files/2016-02/documents/copper_and_copper-alloy_surface_protocol_revised_012916.pdf.

The formulation from Table 2 or the control formulation were applied to separate (but identical) floor surfaces/substrates at 4 g/sqft (950-1000 sqft/gal) over 3 coats of iShine—25% NVS floor finish applied at 2000-3000 sqft/gal/coat and allowed to dry, resulting in a film/coating of 0.4-0.6 mils in thickness on the treated substrate. Test microorganisms (*P. aeruginosa* ATCC: 15442 and *S. aureus* ATCC 6538) were each grown in tryptone soy broth (TSB) for 18-24 hours. Next, each culture was diluted to the target concentration and then supplemented with the tri part (bsa, yeast, mucin) soil load. Next, the treated floor surfaces were inoculated in staggered intervals, with 0.020 ml ($9.40 \times 10^5$ CFU/sample *P. aeruginosa* ATCC 15442 and $3.57 \times 10^5$ CFU/sample *S. aureus* ATCC 6538) of the test culture, and contact times were initiated immediately after inoculation.

Treated substrates (substrates treated with the formulation of Table 2 or a control) having the inoculum placed thereon were allowed to sit for the desired contact times (i.e., 1 hour, 2 hours, and 4 hour time increments). After each respective contact time, the substrates were aseptically harvested in 20 ml of neutralizer according to the EPA Copper Method, and bacterial growth was subsequently measured.

No log reduction in bacterial growth was observed on the control substrates treated with the inoculum. However, on the substrates treated with the formulation of Table 2, a 3.3 log reduction was observed for *P. aeruginosa*, at 1 hour post-application of the inoculum on the treated substrate, a 3.62 log reduction was observed for *P. aeruginosa* at 2 hours post-application of the inoculum on the treated substrate; and a 4.43 log reduction was observed for *P. aeruginosa* at 4 hours post-application of the inoculum on the treated substrate. In addition to the log reduction observed for gram negative bacteria, gram positive bacteria log reductions were concurrently observed on the same substrates. For example, a 3.11 log reduction was observed for *S. aureus* (gram positive bacteria) at 1 hour post-application of the inoculum on the treated substrate; a 3.27 log reduction was observed for *S. aureus* at 2 hours post-application on the inoculum to the treated substrate; and a 3.53 log reduction was observed for *S. aureus* at 4 hours post-application of the inoculum on the treated substrate. Bacterial viability for the above discussed substrate(s) treated with the formulation of Table 2 was as follows: *P. aeruginosa* was $4.73 \times 10^2$ CFU for 1 hour post-application of the inoculum on the treated substrate, $2.25 \times 10^2$ CFU for 2 hours post-application of the inoculum on the treated substrate, and $3.47 \times 10^1$ CFU for 4 hours post-application of the inoculum on the treated substrate, and *S. aureus* was $2.76 \times 10^2$ CFU for 1 hour post-application of the inoculum on the treated substrate, $1.9 \times 10^2$ CFU for 2 hours post-application of the inoculum on the treated substrate, and $1.05 \times 10^2$ CFU for 4 hours post-application of the inoculum on the treated substrate.

Storage Stability

After conducting the above mentioned bench testing and floor application testing, the formulations of Tables 1 and 2 were subjected to storage stability testing conducted at 120° F. for 30 days. This testing not only simulated hot storage tolerance, but also long term storage at room temperature. The formulation of Table 1 exhibited a viscosity increase well over 100% indicating chemical instability when exposed to high temperature(s) for a prolonged time period. During storage stability testing, viscosity of the formulation increased to well above 200 cP. It should be further noted that if viscosity of a floor finish increases above 10 cP, the floor finish cannot be properly applied to the floor and cannot obtain the required finished film aesthetics.

In contrast to the formulation of Table 1, the formulation of Table 2 exhibited adequate storage tolerance (i.e., stability), including maintaining a viscosity of 10 cP or less, when subjected to storage stability testing conducted at 120° F. for 30 days. Regarding heat stability for the formulation of Table 2, it was further determined that the combination of the nonionic oxidized high density polyethylene emulsion and the cationic oxidized high density polyethylene emulsion provided these heat stability characteristics while maintaining mar resistance and limiting viscosity increase of the formulation of Table 2.

The above mentioned test results are generally summarized in Tables A and B shown immediately below.

TABLE A

| | | | JIS Z2801 | | |
|---|---|---|---|---|---|
| | | | 2 hrs | 6 hrs | 24 hrs |
| Results for Substrates Treated With Formulation of Table 1 | *E. coli* | Log$_{10}$ reduction | 4.36 | 4.44 | 5.40 |
| | ATCC 8739 | Bacterial viability | $1.3 \times 10^1$ | $3.4 \times 10^1$ | $6.3 \times 10^1$ |
| | *S. aureus* | Log$_{10}$ reduction | 4.5 | 5.47 | 6.26 |
| | ATCC 6538 | Bacterial viability | $1.0 \times 10^1$ | $1.0 \times 10^1$ | $1.0 \times 10^1$ |

TABLE B

| | | | EPA Copper Method | | |
|---|---|---|---|---|---|
| | | | 1 hr | 2 hrs | 4 hrs |
| Results for Substrates Treated With Formulation of Table 2 | *P. aeruginosa* | Log$_{10}$ reduction | 3.30 | 3.62 | 4.43 |
| | ATCC 15442 | Bacterial viability | $4.73 \times 10^2$ | $2.25 \times 10^2$ | $3.47 \times 10^1$ |
| | *S. aureus* | Log$_{10}$ reduction | 3.11 | 3.27 | 3.53 |
| | ATCC 6538 | Bacterial viability | $2.76 \times 10^2$ | $1.9 \times 10^2$ | $1.05 \times 10^2$ |

Antimicrobial Sacrificial Floor Coating Remover(s)

Shown below in Table 5 is an exemplary antimicrobial sacrificial floor coating remover including water, diethylene glycol monobutyl ether (a first organic solvent), Eastman Omnia™ (CAS Number: 53605-94-0) (a second organic solvent), Tomadol® 91-6 (nonionic surfactant)(CAS Number: 68439-46-3), and Lactic Acid (organic acid) (more particularly L-lactic acid having an 88% purity). This formulation is a concentrated solution including 25.3 wt % actives (i.e., a first and second organic solvent, a nonionic surfactant, and an organic acid) and 74.7 wt % water having a pH of 2.60. As discussed further below, this concentrated solution was subsequently diluted to an operable working concentration and applied to a floor treated with the disclosed antimicrobial sacrificial floor coating of Table 1 and compared to Comparative Examples 1 and 2 (in Tables 6 and 7) to determine efficacy of each remover for removing antimicrobial sacrificial floor coating of Table 1 from a flooring substrate.

TABLE 5

| Exemplary Antimicrobial Sacrificial Floor Coating Remover | |
|---|---|
|  | Weight % |
| Water | 74.7 |
| Diethylene Glycol Monobutyl Ether | 19.3 |
| Eastman Omnia ™ | 3.2 |
| Tomadol ® 91-6 | 1.1 |
| Lactic Acid 88% | 1.7 |

Shown below in Table 6 is Comparative Example 1—a comparative antimicrobial sacrificial floor coating remover including water, diethylene glycol monobutyl ether, Tomadol® 91-6, and phosphoric acid (inorganic acid). The formulation is a concentrated solution including 31.3 wt % actives (i.e., an organic solvent, a nonionic surfactant, and an inorganic acid) and 68.7 wt % water having a pH of 1.1. As discussed further below, this concentrated solution was diluted to an operable working concentration and applied to a floor treated with the disclosed antimicrobial sacrificial floor coating of Table 1 and compared to the Exemplary Antimicrobial Sacrificial Floor Coating Remover of Table 5 and Comparative Example 2 of Table 7 to determine efficacy of each remover for removing antimicrobial sacrificial floor coating of Table 1 from a flooring substrate.

TABLE 6

| Comparative Example 1 | |
|---|---|
|  | Weight % |
| Water | 68.7 |
| Diethylene Glycol Monobutyl Ether | 19.9 |
| Tomadol ® 91-6 | 1.0 |
| Phosphoric Acid (75%) | 10.4 |

Shown below in Table 7 is Comparative Example 2—a comparative antimicrobial sacrificial floor coating remover including substantially the same chemical components as the Exemplary Antimicrobial Sacrificial Floor Coating Remove of Table 5 but excluding the organic acid. Specifically, Comparative Example 2 includes water, diethylene glycol monobutyl ether (a first organic solvent), Eastman Omnia™ (CAS Number: 53605-94-0) (a second organic solvent), and Tomadol® 91-6 (nonionic surfactant). This formulation is a concentrated solution including 34.1 wt % actives (i.e., a first and second organic solvent, and a nonionic surfactant) and 65.9 wt % water having a pH of 5.9. As discussed further below, this concentrated solution was diluted to an operable working concentration and applied to a floor treated with the disclosed antimicrobial sacrificial floor coating of Table 1 and compared to the Exemplary Antimicrobial Sacrificial Floor Coating Remover of Table 5 and Comparative Example 1 of Table 6 to determine efficacy of each remover for removing antimicrobial sacrificial floor coating of Table 1 from a flooring substrate.

TABLE 7

| Comparative Example 2 | |
|---|---|
|  | Weight % |
| Water | 65.9 |
| Diethylene Glycol Monobutyl Ether | 22.0 |
| Eastman Omnia ™ | 11.0 |
| Tomadol ® 91-7 | 1.1 |

Dilution of Antimicrobial Sacrificial Floor Coating Remover(s)

Each of the concentrated solutions (shown in Tables 5-7) were subsequently diluted to a working concentration for application to and to further observe efficacy of removing the antimicrobial sacrificial floor coating of Table 1 from floors/flooring substrates. Specifically, each concentrated solution was diluted with 1 part concentrated solution to 5 parts water (1:5) and mixed to obtain a homogeneous working solution. The pH of the diluted Exemplary Antimicrobial Sacrificial Floor Coating Remover of Table 5 (working solution) was 2.8. The pH of the diluted Comparative Example 1 of Table 6 (working solution) was 1.6. The pH of the diluted Comparative Example 2 of Table 7 (working solution) was 7.4.

Application of Diluted Antimicrobial Sacrificial Floor Coating Remover(s)

After obtaining working solutions for each of the formulations in Tables 5-7, each working solution was applied to a flooring substrate previously treated with the antimicrobial sacrificial floor coating of Table 1 and 2. Specifically, the flooring substrate included a 0.33 mil antimicrobial sacrificial floor coating applied over three coats of a conventional, zinc crosslinked floor finish.

Each working solution was applied to a floor substrate having the antimicrobial sacrificial floor coating at 0.33 mil thickness for 5 minutes (dwell time). Post-application and allowing for the above mentioned dwell time, the antimicrobial sacrificial floor coating of the flooring substrate treated with the working solution of the formulation from Table 5 swelled to approximately 1.188 mil thickness and was subsequently removed by manual scrubbing with a scrubbing pad for 3-5 seconds/sqft. This process could be repeated as desired, and the antimicrobial sacrificial floor coating of Table 1 and 2 could then be reapplied to the flooring substrate if desired.

Unlike the working solution using the exemplary antimicrobial sacrificial floor coating remover of Table 5, each working solutions using Comparative Example 1 and 2 was ineffective for removing the antimicrobial sacrificial floor coating from the flooring substrate. Specifically, Comparative Example 1 attacked the sacrificial antimicrobial floor coating, but did not allow lifting or abrading off the substrate. The film became cloudy and clearly reacted with the remover, but removal of the film was not possible/achieved. Comparative Example 2 did not exhibit any change in appearance or removal. After the dwell and scrub, the coating was completely intact, as if no removal was attempted.

The foregoing description provides embodiments of the invention by way of example only. It is envisioned that other embodiments may perform similar functions and/or achieve similar results. Any and all such equivalent embodiments and examples are within the scope of the present invention and are intended to be covered by the appended claims.

What is claimed is:

1. An antimicrobial sacrificial floor coating composition comprising:
   (a) a nonionic acrylic polymer;
   (b) a nonionic wax;
   (c) a cationic wax; and
   (d) an antimicrobial agent that includes a cationic alkyl biguanide or salt thereof, wherein:
   the antimicrobial sacrificial floor coating composition has a pH of less than 7, and
   the antimicrobial sacrificial floor coating composition is adapted to form a clear, thin film coating having a thickness ranging from 0.2 mils to 1.1 mils that exhibits continuous antimicrobial properties from full cure on a floor surface up to 1 year post-application to the floor surface at a minimum contact time of 1 hour.

2. The antimicrobial sacrificial floor coating composition of claim 1, wherein the antimicrobial sacrificial floor coating composition is adapted to exhibit a log reduction of from 3.3 to 6 for gram negative bacteria and a log reduction of from 3.11 to 6.3 for gram positive bacteria after full cure on the flooring surface and at a minimum contact time of 1 hour with the coating composition.

3. The antimicrobial sacrificial floor coating composition of claim 1, wherein the antimicrobial sacrificial floor coating composition is heat stable and maintains a viscosity ranging from 4 to 6 cP when exposed to 120° F. for 20 to 30 days.

4. The antimicrobial sacrificial floor coating composition of claim 1, wherein the nonionic wax is a nonionic alkylene polymer.

5. The antimicrobial sacrificial floor coating composition of claim 4, wherein the nonionic wax is a high density polyethylene or derivative thereof, a high density polypropylene or derivative thereof, or a combination thereof.

6. The antimicrobial sacrificial floor coating composition of claim 5, wherein the nonionic wax is an oxidized high density polyethylene at a concentration of between 2.5 wt % to 8 wt % in the antimicrobial sacrificial floor coating composition and has a molecular weight ranging between 9000 to 10,000 g/mol.

7. The antimicrobial sacrificial floor coating composition of claim 1, wherein the cationic wax is a cationic alkylene polymer.

8. The antimicrobial sacrificial floor coating composition of claim 7, wherein the cationic alkylene polymer is an oxidized high density polyethylene, an oxidized high density oxidized polypropylene, or a combination thereof.

9. The antimicrobial sacrificial floor coating composition of claim 8, wherein the cationic alkylene polymer is a cationic oxidized high density polyethylene at a concentration of between 2.5 wt % to 8.0 wt % in the antimicrobial sacrificial floor coating composition and has a molecular weight ranging from 1,000 to 50,000 g/mol.

10. The antimicrobial sacrificial floor coating composition of claim 1, wherein the cationic alkyl biguanide or salt thereof is polyhexamethylene biguanide, polyaminopropryl biguanide, or a combination thereof.

11. The antimicrobial sacrificial floor coating composition of claim 10, wherein cationic alkyl biguanide or salt thereof ranges from 0.4 to 1 active wt % in the antimicrobial sacrificial floor coating.

12. The antimicrobial sacrificial floor coating composition of claim 1, wherein the antimicrobial sacrificial floor coating does not include crosslinking agents and is not polymerizable during or post-application to a floor surface.

13. The antimicrobial sacrificial floor coating composition of claim 1, wherein the antimicrobial sacrificial floor coating composition consists of:
   (a) the nonionic acrylic polymer at a concentration ranging from 30 to 40 wt % of the antimicrobial sacrificial floor coating composition;
   (b) the nonionic wax at a concentration ranging from 2.5 to 8 wt % of the antimicrobial sacrificial floor coating composition,
   (c) the cationic wax at a concentration ranging from 2.5 to 8 wt % of the antimicrobial sacrificial floor coating composition;
   (d) the antimicrobial agent being present at a concentration of up to 4 wt % of the antimicrobial sacrificial floor coating composition;
   (e) water at a concentration ranging from 30 to 65 wt % of the antimicrobial sacrificial floor coating composition; and
   (f) at least one additive, wherein:
   the antimicrobial sacrificial floor coating composition has a pH of less than 7.

14. The antimicrobial sacrificial floor coating composition of claim 13, wherein the antimicrobial sacrificial floor coating composition exhibits a log reduction of from 3.3 to 6 for gram negative bacteria and a log reduction of 3.11 to 6.3 for gram positive bacteria after full cure on the flooring surface and at a minimum contact time of 1 hour with the coating composition.

15. An antimicrobial sacrificial floor coating remover comprising:
   (a) an organic solvent at a concentration ranging from 17 wt % to 30 wt % of the antimicrobial sacrificial floor coating remover;
   (b) a nonionic surfactant at a concentration ranging from 0.5 wt % to 5 wt % of the antimicrobial sacrificial floor coating remover; and
   (c) an organic acid at a concentration ranging from 1 wt % to 5 wt % of the antimicrobial sacrificial floor coating remover, wherein:
   pH of the antimicrobial sacrificial floor coating remover is acidic.

16. The antimicrobial sacrificial floor coating remover of claim 15, further comprising water at a concentration ranging from 60 wt % to 80 wt % of the antimicrobial sacrificial floor coating remover.

17. The antimicrobial sacrificial floor coating remover of claim 15, wherein the pH of the antimicrobial sacrificial floor coating remover ranges from 2 to 3.5.

18. The antimicrobial sacrificial floor coating remover of claim 15, wherein the organic acid comprises a lower alkyl carboxylic acid moiety.

19. The antimicrobial sacrificial floor coating remover of claim 18, wherein the lower alkyl carboxylic acid moiety is R—COOH in which R is hydrogen, a linear or branched C1-C6 alkyl, a primary alcohol, or a secondary alcohol.

20. The antimicrobial sacrificial floor coating remover of claim 19, wherein the organic acid is propanoic acid or a derivative thereof.

21. The antimicrobial sacrificial floor coating remover of claim 19, wherein the organic acid is lactic acid.

22. The antimicrobial sacrificial floor coating remover of claim 21, wherein the organic acid is L-lactic acid.

23. The antimicrobial sacrificial floor coating remover of claim 15, wherein the nonionic surfactant comprises a linear alcohol ethoxylate at a concentration ranging from 0.5 wt % to 5 wt % of the antimicrobial sacrificial floor coating remover.

24. The antimicrobial sacrificial floor coating remover of claim 23, wherein the linear alcohol ethoxylate is a C9-C11 linear alcohol ethoxylate.

25. The antimicrobial sacrificial floor coating remover of claim 15, wherein the organic solvent includes a first organic solvent that is a glycol ether at a concentration ranging from 16 to 25 wt % of the antimicrobial sacrificial floor coating remover and a second organic solvent at a concentration ranging from 1 to 7 wt % of the antimicrobial sacrificial floor coating remover.

26. The antimicrobial sacrificial floor coating remover of claim 25, wherein the glycol ether is diethylene glycol monobutyl ether.

27. The antimicrobial sacrificial floor coating remover of claim 15, wherein the antimicrobial sacrificial floor coating remover has a zero volatile organic compound (0 VOC) content.

28. A kit comprising:
(i) an antimicrobial sacrificial floor coating composition in a first container, the antimicrobial sacrificial floor coating composition having a pH of less than 7 and comprising:
(a) a nonionic acrylic polymer;
(b) a nonionic wax;
(c) a cationic wax; and
(d) an antimicrobial agent that includes a cationic alkyl biguanide or salt; and
(ii) an antimicrobial sacrificial floor coating remover in a second container, the antimicrobial sacrificial floor coating remover being acidic and comprising:
(a) an organic solvent at a concentration ranging from 17 wt % to 30 wt % of the antimicrobial sacrificial floor coating remover;
(b) a nonionic surfactant at a concentration ranging from 0.5 wt % to 5 wt % of the antimicrobial sacrificial floor coating remover; and
(c) an organic acid at a concentration ranging from 1 wt % to 5 wt % of the antimicrobial sacrificial floor coating remover.

29. The kit of claim 28, wherein the antimicrobial sacrificial floor coating remover further comprises water.

30. The kit of claim 29, wherein the antimicrobial sacrificial floor coating remover has a zero volatile organic compound (0 VOC) content.

31. An antimicrobial sacrificial floor coating composition comprising:
(a) an acrylic polymer;
(b) a nonionic wax;
(c) a cationic wax; and
(d) an antimicrobial agent that includes a cationic alkyl biguanide or salt thereof, wherein:
the antimicrobial sacrificial floor coating composition has a pH of less than 7, and
the antimicrobial sacrificial floor coating composition is adapted to form a clear, thin film coating having a thickness ranging from 0.2 mils to 1.1 mils that exhibits continuous antimicrobial properties from full cure on a floor surface up to 1 year post-application to the floor surface at a minimum contact time of 1 hour.

32. The antimicrobial sacrificial floor coating composition of claim 31, wherein the antimicrobial sacrificial floor coating composition is adapted to exhibit a log reduction of from 3.3 to 6 for gram negative bacteria and a log reduction of from 3.11 to 6.3 for gram positive bacteria after full cure on the flooring surface and at a minimum contact time of 1 hour with the coating composition.

33. The antimicrobial sacrificial floor coating composition of claim 31, wherein the antimicrobial sacrificial floor coating composition is heat stable and maintains a viscosity ranging from 4 to 6 cP when exposed to 120° F. for 20 to 30 days.

34. The antimicrobial sacrificial floor coating composition of claim 31, wherein the nonionic wax is a nonionic alkylene polymer.

35. The antimicrobial sacrificial floor coating composition of claim 34, wherein the nonionic wax is a high density polyethylene or derivative thereof, a high density polypropylene or derivative thereof, or a combination thereof.

36. The antimicrobial sacrificial floor coating composition of claim 35, wherein the nonionic wax is an oxidized high density polyethylene at a concentration of between 2.5 wt % to 8 wt % in the antimicrobial sacrificial floor coating composition and has a molecular weight ranging between 9000 to 10,000 g/mol.

37. The antimicrobial sacrificial floor coating composition of claim 31, wherein the cationic wax is a cationic alkylene polymer.

38. The antimicrobial sacrificial floor coating composition of claim 37, wherein the cationic alkylene polymer is an oxidized high density polyethylene, an oxidized high density oxidized polypropylene, or a combination thereof.

39. The antimicrobial sacrificial floor coating composition of claim 38, wherein the cationic alkylene polymer is a cationic oxidized high density polyethylene at a concentration of between 2.5 wt % to 8.0 wt % in the antimicrobial sacrificial floor coating composition and has a molecular weight ranging from 1,000 to 50,000 g/mol.

40. The antimicrobial sacrificial floor coating composition of claim 31, wherein the cationic alkyl biguanide or salt thereof is polyhexamethylene biguanide, polyaminopropryl biguanide, or a combination thereof.

41. The antimicrobial sacrificial floor coating composition of claim 40, wherein cationic alkyl biguanide or salt thereof ranges from 0.4 to 1 active wt % in the antimicrobial sacrificial floor coating.

42. The antimicrobial sacrificial floor coating composition of claim 31, wherein the antimicrobial sacrificial floor coating does not include crosslinking agents and is not polymerizable during or post-application to a floor surface.

43. The antimicrobial sacrificial floor coating composition of claim 31, wherein the antimicrobial sacrificial floor coating composition consists of:
(a) the acrylic polymer at a concentration ranging from 30 to 40 wt % of the antimicrobial sacrificial floor coating composition;
(b) the nonionic wax at a concentration ranging from 2.5 to 8 wt % of the antimicrobial sacrificial floor coating composition,
(c) the cationic wax at a concentration ranging from 2.5 to 8 wt % of the antimicrobial sacrificial floor coating composition;
(d) the antimicrobial agent being present at a concentration of up to 4 wt % of the antimicrobial sacrificial floor coating composition;
(e) water at a concentration ranging from 30 to 65 wt % of the antimicrobial sacrificial floor coating composition; and
(f) at least one additive, wherein:
the antimicrobial sacrificial floor coating composition has a pH of less than 7.

44. The antimicrobial sacrificial floor coating composition of claim 43, wherein the antimicrobial sacrificial floor coating composition exhibits a log reduction of from 3.3 to 6 for gram negative bacteria and a log reduction of 3.11 to 6.3 for gram positive bacteria after full cure on the flooring surface and at a minimum contact time of 1 hour with the coating composition.

* * * * *